United States Patent
Mucha et al.

(10) Patent No.: US 9,765,358 B2
(45) Date of Patent: Sep. 19, 2017

(54) METHOD FOR PRODUCING CHIMERIC MICROBIAL HYBRIDS

(71) Applicant: SciBac Inc., Milpitas, CA (US)

(72) Inventors: Jeanette M. Mucha, San Carlos, CA (US); Anthony F. Cann, San Francisco, CA (US)

(73) Assignee: SciBac Inc., Milpitas, CA (US)

( * ) Notice: Subject to any disclaimer, the term of this patent is extended or adjusted under 35 U.S.C. 154(b) by 0 days.

(21) Appl. No.: 15/212,068

(22) Filed: Jul. 15, 2016

(65) Prior Publication Data

US 2017/0137844 A1    May 18, 2017

Related U.S. Application Data

(60) Provisional application No. 62/256,625, filed on Nov. 17, 2015.

(51) Int. Cl.
| | |
|---|---|
| *C12P 1/00* | (2006.01) |
| *C12P 39/00* | (2006.01) |
| *C12N 1/00* | (2006.01) |
| *C12N 1/20* | (2006.01) |
| *C12N 15/87* | (2006.01) |
| *C12N 1/16* | (2006.01) |

(52) U.S. Cl.
CPC .............. *C12N 15/87* (2013.01); *C12N 1/16* (2013.01); *C12N 1/20* (2013.01); *C12N 2502/70* (2013.01)

(58) Field of Classification Search
CPC ........ C12N 15/867; C12N 15/86; C12N 1/15; C12N 1/19; C12N 1/21; C12N 5/00; C07K 14/78; C07K 14/00; C07K 14/47; C07K 14/705; C07K 16/18; A01K 67/027; A01K 67/033; A61K 31/7088; A61K 38/00; A61K 39/395; A61K 45/00; A61K 48/00; A61P 35/00; A61P 43/00; C07H 21/00

See application file for complete search history.

(56) References Cited

PUBLICATIONS

Oyarzabal et al., (J. of Clin. Microbio.Feb. 2007. vol. 45(2):402-408).*
Nevoigt et al., (Yeast. Jul. 2000. vol. 16, Issue 12. pp. 1107-1110).*
Aminov. Front. Microbio. Jul. 2011. vol. 2. Article 158. pp. 1-19.*
Eyre-Walker, A., et al., The distribution of fitness effects of new mutations, Nature Reviews Genetics, 2007, 8:610-618ac.
Schaeffer, P., et al., Fusion of bacterial protoplasts, Proc. Natl. Acad. Sci. USA, 1976, 73(6):2151-2155.
De la Cruz, F., et al., Horizontal gene transfer and the origin of species: lessons from bacteria, Trends in Microbiology, 2000, 8(3):128-133.
Davies, J., Inactivation of Antibiotics and the Dissemination of Resistance Genes, Science, 1994, 264:375-382.
Bertram, J., et al., Natural Transfer of Conjugative Transposon Tn916 between Gram-Positive and Gram-Negative Bacteria, Journal of Bacteriology, 1991, 173(2):443-448.

(Continued)

*Primary Examiner* — Ja'na Hines
(74) *Attorney, Agent, or Firm* — Jill A. Jacobson

(57) ABSTRACT

Described is a method to transfer chromosomal DNA between two microbial species without genetic engineering or vectors. The strains resulting from this method are chimeric microbial hybrids that can express a combination of genotypes from both parents.

21 Claims, 9 Drawing Sheets

(56) References Cited

PUBLICATIONS

Huang, M., Accuracy of the E Test for Determining Antimicrobial Susceptibilities of *Staphylococci, Enterococci, Campylobacter jejuni*, and Gram-Negaive Bacteria Resistant to Antimicrobial Agents, Journal of Clinical Microbiology, 1992, 30(12):3243-3248.

Kim, J., Distribution of Antibiotic MICs for *Helicobacter pylori* Strains over a 16-Year Period in Patients from Seoul, South Korea, Antimicrobial Agents and Chemotherapy, 2004, 48(12): 4843-4847.

Ieela, F., Transfer of the chromosomally encoded tetracycline resistance gene tet(M) from marine bacteria to *Escherichia coli* and *Enterococcus faecalis*, World J Mlcrobiol Biotechnol, 2009, 25:1095-1101.

\* cited by examiner

FIGURES 1A – 1E
Parental Donor
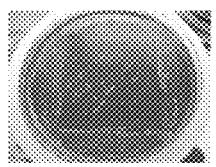
Figure 1A
Parental Host
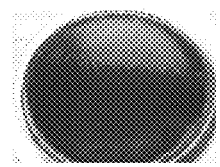
Figure 1B
Chimeric Hybrids:
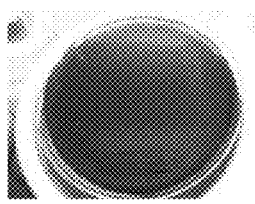
Figure 1C
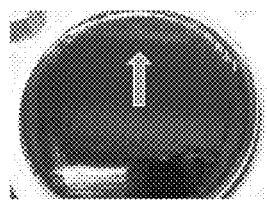
Figure 1D
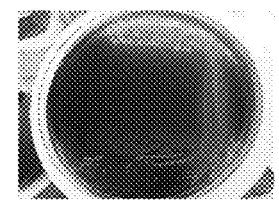
Figure 1E
FIGURES 2A – 2E
Parental Donor
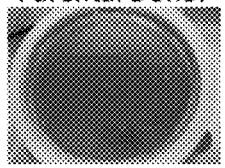
Figure 2A
Parental Host
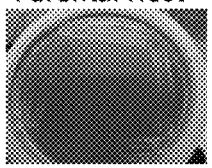
Figure 2B
Chimeric Hybrids:
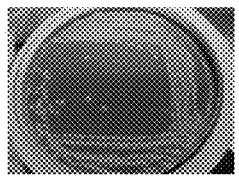
Figure 2C
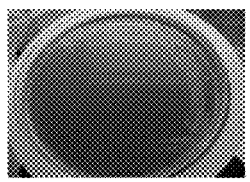
Figure 2D
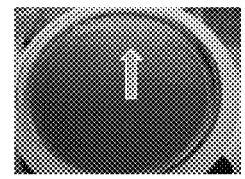
Figure 2E

FIGURES 3A – 3C

|  | Phenotype | L-Arabinose | D-Ribose | D-Xylose | Methyl-βD-Xylopyranoside | D-Galactose | D-Glucose | D-Fructose | D-Mannose | L-Rhamnose | Inositol | D-Mannitol | D-Sorbitol |
|---|---|---|---|---|---|---|---|---|---|---|---|---|---|
| P-C.b. | clostridium | X |  | X | X |  | X | X | X |  | X | X | X |
| P-L.p. | lactobacillus |  | X |  |  | X | X | X | X | X |  | X |  |
| C-1 (EtOH P-S) | clostridium | X | X |  |  | X |  |  |  |  |  |  |  |
| C-2 (no P-S) | lactobacillus | X |  | X | X | X |  |  |  | X |  |  | X |
| C-3 (no P-S) | lactobacillus |  | X | X | X | X |  |  |  |  |  |  | X |
| C-4 (LB only UV P-S) | lactobacillus | X | X | X | X | X |  |  |  | X | X |  | X |
| C-5 (LB & CL UV P-S) | lactobacillus | X |  | X | X | X |  |  |  | X | X |  | X |
| C-6 (LB & CL UV P-S) | lactobacillus | X |  | X | X | X |  |  |  | X | X |  | X |
| C-7 (LB & CL UV P-S) | lactobacillus | X |  | X | X | X |  |  |  | X | X |  | X |
| C-8 (LB & CL UV P-S) | lactobacillus | X |  | X | X | X |  |  |  | X | X |  | X |
| C-9 (no P-S) | both | X |  | X | X | X |  |  |  | X | X |  | X |
| C-10 (LB & CL UV P-S) | lactobacillus | X |  | X | X | X |  |  |  | X | X |  | X |

Figure 3A

|  | Phenotype | Methyl-αD-Mannopyranoside | Methyl-αD-N-Glucopyranoside | AcetylGlucosamine | Amygdalin | Arbutin | Esculin | Salicin | D-Cellobiose | D-Maltose | Lactose | D-Melibiose | Sucrose |
|---|---|---|---|---|---|---|---|---|---|---|---|---|---|
| P-C.b. | clostridium |  | X | X | X |  | X | X | X | X | X | X | X |
| P-L.p. | lactobacillus | X | X | X | X | X | X | X | X | X | X | X | X |
| C-1 (EtOH P-S) | clostridium |  |  | X |  |  |  |  |  |  |  |  |  |
| C-2 (no P-S) | lactobacillus | X |  |  |  | X |  |  |  |  |  |  |  |
| C-3 (no P-S) | lactobacillus | X |  |  |  | X |  |  |  |  |  |  |  |
| C-4 (LB only UV P-S) | lactobacillus | X |  |  |  | X |  |  |  |  |  |  |  |
| C-5 (LB & CL UV P-S) | lactobacillus | X |  |  |  | X |  |  |  |  |  |  |  |
| C-6 (LB & CL UV P-S) | lactobacillus | X |  |  |  | X |  |  |  |  |  |  |  |
| C-7 (LB & CL UV P-S) | lactobacillus | X |  |  |  | X |  |  |  |  |  |  |  |
| C-8 (LB & CL UV P-S) | lactobacillus | X |  |  |  | X |  |  |  |  |  |  |  |
| C-9 (no P-S) | both | X |  |  |  | X |  |  |  |  |  |  |  |
| C-10 (LB & CL UV P-S) | lactobacillus | X |  |  |  | X |  |  |  |  |  |  |  |

Figure 3B

|  | Phenotype | D-Trehalose | Inulin | D-Melezitose | D-Raffinose | Amidon (Starch) | Glycogen | Gentiobiose | D-Turanose | D-Arabitol | L-Arabitol | Potassium Gluconate |
|---|---|---|---|---|---|---|---|---|---|---|---|---|
| P-C.b. | clostridium | X | X |  |  | X | X |  | X | X | X |  |
| P-L.b. | lactobacillus | X |  | X | X |  |  | X | X | X |  |  |
| C-1 (EtOH P-S) | clostridium |  |  |  |  | X |  |  |  |  |  |  |
| C-2 (no P-S) | lactobacillus |  |  | X | X | X | X | X |  |  |  | X |
| C-3 (no P-S) | lactobacillus |  |  | X | X | X | X | X |  |  |  | X |
| C-4 (LB only UV P-S) | lactobacillus |  |  | X | X | X | X | X |  |  |  | X |
| C-5 (LB & CL UV P-S) | lactobacillus |  |  | X | X | X | X | X |  |  |  | X |
| C-6 (LB & CL UV P-S) | lactobacillus |  |  | X |  | X | X | X |  |  | X | X |
| C-7 (LB & CL UV P-S) | lactobacillus | X |  | X | X | X | X | X |  | X | X | X |
| C-8 (LB & CL UV P-S) | lactobacillus |  |  | X | X | X | X | X |  |  |  | X |
| C-9 (no P-S) | both |  |  | X | X | X | X | X |  |  |  | X |
| C-10 (LB & CL UV P-S) | lactobacillus |  |  | X | X | X | X | X |  | X | X | X |

Figure 3C

KEY: = P-L.p. and P-C.b. shared trait | X = P-L.p. only trait | X = P-C.b. only trait | X = chimeric hybrid only trait

FIGURES 4A – 4D
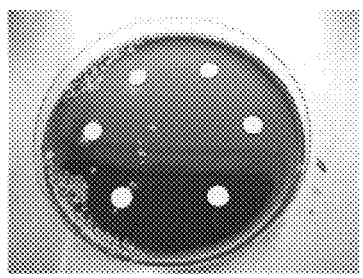
Figure 4A
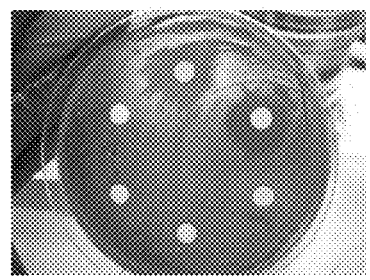
Figure 4B
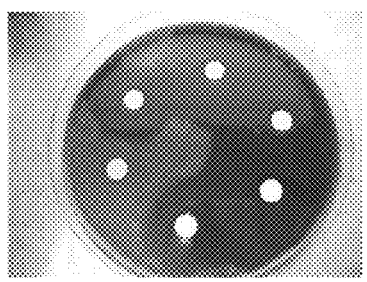
Figure 4C
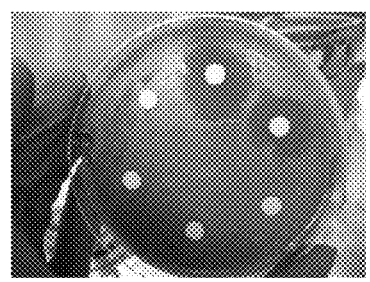
Figure 4D
FIGURE 5
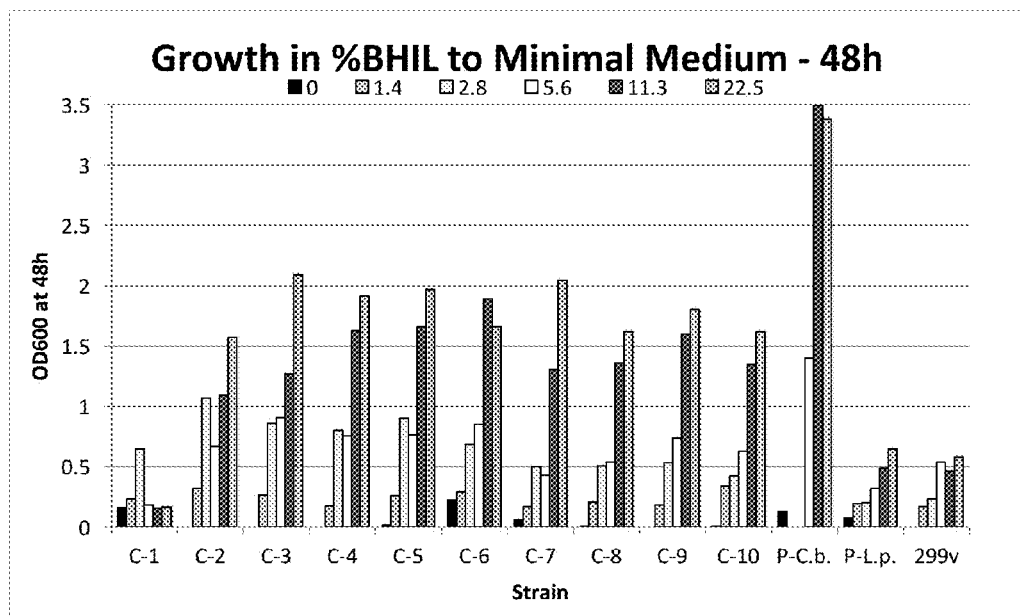

FIGURES 8A – 8D
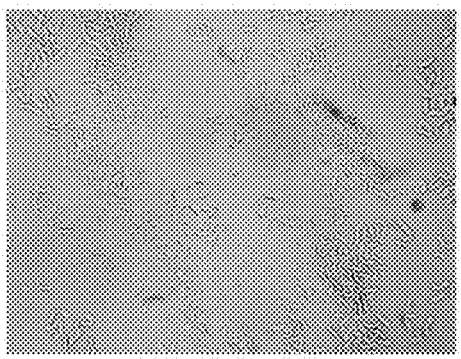
FIGURE 8A
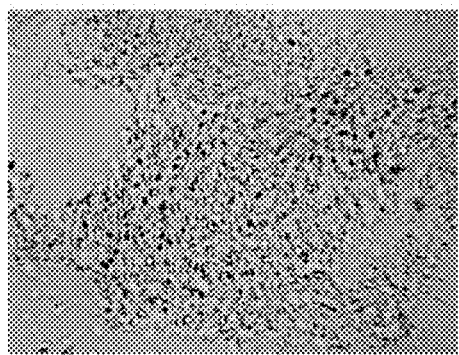
FIGURE 8B
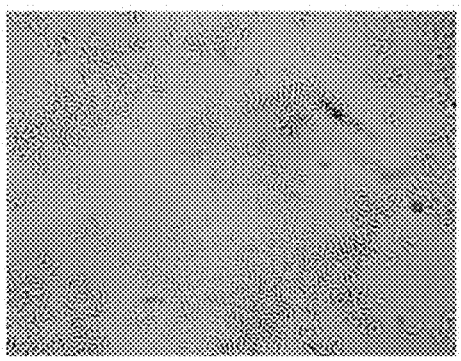
FIGURE 8C
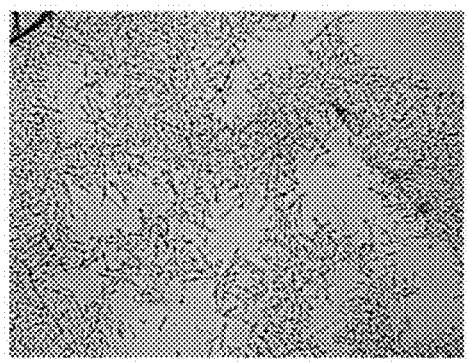
FIGURE 8D
FIGURES 9A – 9B
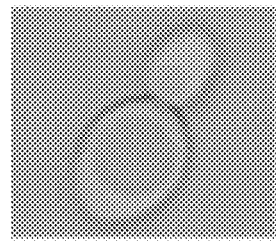
FIGURE 9A
Regular budding
ideal conditions
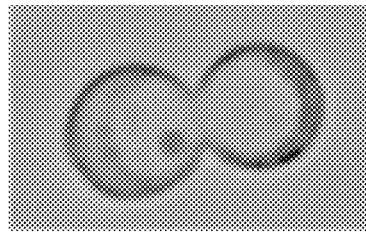
FIGURE 9B
Gene transfer formation
in stressed cultures

FIGURE 10A 30-31C

| 72h | Glucose | Glycerol | Ca 2-Keto-Gluconate | L-arabinose | D-Xylose | Adonitol | Xylitol | D-Galactose | Inositol | D-Sorbitol |
|---|---|---|---|---|---|---|---|---|---|---|
| M. reukafii | ++ | ++ | ++ | | | + | ++ | + | | ++ |
| S. boulardii | ++ | + | + | | | | | + | + | |
| | | | | | | | | | | |
| YC-1 (UV PS) | ++ | + | | | | | + | | | + |
| YC-2 (UV PS) | ++ | + | + | | | | | + | | ++ |
| YC-3 (UV PS) | ++ | + | + | | | | | | | |
| YC-4 (UV PS) | ++ | | | | | | | | | |
| YC-5 (UV PS) | ++ | + | + | | | | + | + | + | + |
| YC-6 (UV PS) | ++ | | + | | | | | | | |
| YC-7 (no PS) | ++ | + | | | | | | + | | + |
| YC-8 (no PS) | ++ | + | + | | | | | + | + | + |
| YC-9 (no PS) | + | | + | | | | | + | | |
| YC-10 (no PS) | ++ | + | + | | | | | ++ | | |
| YC-11 (no PS) | ++ | + | + | | | | + | + | | + |
| KEY | SB82 ONLY | | SB84 ONLY | | BOTH PARENTS | | ++ indicates dense growth<br>+ indicates light growth | | | |

FIGURE 10B

| 72h | Methyl-αD-Glucopyranoside | N-Acetyl-Glucosamine | D-Cellobiose | D-Lactose | D-Maltose | D-Saccharose | D-Trehalose | D-Melezitose | D-Raffinose |
|---|---|---|---|---|---|---|---|---|---|
| M. reukafii | + | ++ | ++ |  | ++ | ++ | + | ++ |  |
| S. boulardii |  | + | + | + | ++ | ++ | + | ++ | ++ |
|  |  |  |  |  |  |  |  |  |  |
| YC-1 (UV PS) | + | + | + | + | ++ | ++ | ++ | + | ++ |
| YC-2 (UV PS) | + | + | + | + | ++ | ++ | + | + | ++ |
| YC-3 (UV PS) |  |  |  |  |  | + |  |  |  |
| YC-4 (UV PS) |  |  | + | + | ++ | ++ |  |  | ++ |
| YC-5 (UV PS) | + | + | + | + | ++ | ++ | ++ | + | ++ |
| YC-6 (UV PS) |  |  |  |  |  | ++ |  |  |  |
| YC-7 (no PS) | + | + | + | + | ++ | ++ | ++ | + | ++ |
| YC-8 (no PS) | + | + | + | + | ++ | ++ | ++ | + | ++ |
| YC-9 (no PS) |  |  |  | + | + | + |  |  |  |
| YC-10 (no PS) |  |  |  |  | ++ | ++ | + | + | ++ |
| YC-11 (no PS) | + | + | + | + | ++ | ++ | ++ | + | ++ |
| KEY | SB82 ONLY | | SB84 ONLY | | BOTH PARENTS | | ++ indicates dense growth | | |
| | | | | | | | + indicates light growth | | |

FIGURES 12A – 12C

| Strain | 16s rRNA | L-Arabinose | Ribose | D-Xylose | Methyl-BD-Xylopyranoside | D-Galactose | D-Glucose | D-Fructose | D-Mannose | D-Mannitol |
|---|---|---|---|---|---|---|---|---|---|---|
| G. senegalensis parent | G. senegalensis | X | | X | X | X | X | X | X | X |
| B. faecale parent | B. faecale | | X | | | X | X | X | | |
| C-5 | B. faecale | X | X | X | | X | X | X | | |
| C-7 | B. faecale | X | X | X | | X | X | X | | |
| C-9 | B. faecale | X | X | X | | X | X | X | | X |
| KEY | | X = Shared parental trait | X | = Bifido | | X | = Grimontella | | X | = hybrid |

FIGURE 12A

| Strain | 16s rRNA | D-Sorbitol | Methyl-αD-Glucopyranoside | N-AcetylGlucosamine | Arbutin | Esculin | Salicin | D-Cellobiose | D-Maltose | D-Lactose |
|---|---|---|---|---|---|---|---|---|---|---|
| G. senegalensis parent | G. senegalensis | X | | X | | X | X | X | X | X |
| B. faecale parent | B. faecale | | X | X | | X | X | | X | X |
| C-5 | B. faecale | | X | | | X | X | | X | X |
| C-7 | B. faecale | | X | | | X | | | | X |
| C-9 | B. faecale | | X | | X | X | X | | X | X |
| KEY | | X = Shared parental trait | X | = Bifido | | X | = Grimontella | | X | = hybrid |

FIGURE 12B

| Strain | 16s rRNA | D-Melibiose | Sucrose | D-Trehalose | Inulin | D-Raffinose | Amidon (Starch) | Glycogen | Gentiobiose |
|---|---|---|---|---|---|---|---|---|---|
| G. senegalensis parent | G. senegalensis | | X | X | | | X | | X |
| B. faecale parent | B. faecale | | | | | X | | X | |
| C-5 | B. faecale | | | | | X | X | X | |
| C-7 | B. faecale | X | X | | X | X | X | X | |
| C-9 | B. faecale | X | | | X | X | X | X | |
| KEY | | X = Shared parental trait | X | = Bifido | | X | = Grimontella | | X | = hybrid |

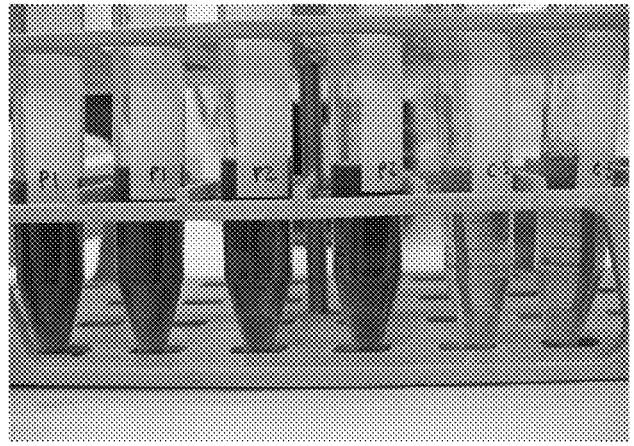

METHOD FOR PRODUCING CHIMERIC MICROBIAL HYBRIDS

CROSS-REFERENCE TO RELATED APPLICATIONS

This application claims the benefit of U.S. Provisional Application No. 62/256,625, filed on Nov. 17, 2015, which is incorporated by reference herein in its entirety.

FIELD OF THE INVENTION

The invention relates to a method to transfer chromosomal DNA between two microbial species without genetic engineering, in particular a method that may be used to add or delete phenotypes by horizontal gene transfer without the use of a vector. The strains resulting from this method are chimeric microbial hybrids that can express a combination of DNA from both parents.

BACKGROUND

Bacteria and fungi have a variety of commercial applications and are used in the production of alcoholic beverages, food products, pesticides, food additives, biofuels, probiotics, and pharmaceuticals. Microbes with a combination of phenotypic traits that are not commonly encountered in nature are often required for some applications, such as biotherapeutics. Wild-type microbial strains show evolutionary development for survival and reproduction. However, commercial applications often require strains with a mixture of traits that both optimize the industrial process and produce products in amounts that are often not advantageous within the microbe's natural environment. Strain alteration and improvement methods were developed to create new commodities and/or increase profitability. Traditional strain alteration is dominated by three different approaches, each with its own limitations, as described below.

The first, classical mutagenesis, relies on chemically induced point and shift mutations of existing genes. Most of these mutations are neutral or even deleterious (Eyre-Walker, et al. (2007) *Nature Reviews Genetics* 8:610-618). The resulting mutations are completely random, and desired strains are found by using selective medium after a mutagen is applied. One limitation is that mutagenesis cannot be used to add exogenous genes from other strains or species. In addition, repeated rounds of mutagenesis can be subject to "Muller's Ratchet," which is the process by which the genomes of an asexual population accumulate deleterious mutations in an irreversible manner. Each new round of mutagenesis makes finding a viable, improved mutant more difficult due to the accumulation of deleterious mutations. Other strain improvement methods include recombination, which helps to avoid Muller's Ratchet.

The second method of strain alteration is recombination, in which hybrids are formed through techniques such as protoplast fusion. This technique fuses two different strains together by first removing the parents' cell walls and then fusing the resulting protoplasts together through spontaneous or induced fusion. This can create microbes and plants with polyploidy that sometimes have greater productivity than the individual parent strains. This method allows the recombination of strains that may not normally conjugate, and is useful when target genes are unknown or a polygenic trait needs to be transferred. The fusion results in the combination of both parents' entire genomes. It is a method that has been most successfully used for the alteration of crop plants and molds that function well with polyploidy. In some yeast, karyogamy usually occurs a few generations later, whereupon one of the transferred nuclei can be lost before recombination has occurred. Protoplast fusion has been unsuccessful for gram negative bacteria and although there has been some success with protoplast fusion in gram positive bacteria, the success rate is extremely low so it is not often used. There is a low success rate of hybrid formation between strains of the same species, such as *Bacillus subtilis* (Schaeffer, P. et al (1976) *Proc Natl Acad Sci* 73(6):2151-2155). Protoplasts were first formed at the rate of $2.5 \times 10^{-8}$ from initial wild-type cell cultures. Then, protoplasts were fused to create hybrids at a maximum rate of $4 \times 10^{-3}$ per pairing of parent protoplasts. This means the best final frequency of hybrids per one original parent cell is only $6.4 \times 10^{-12}$. Combining protoplasts from different species has an even lower success rate and in most cases is not a reliable or economically viable option for horizontal gene transfer in bacteria.

The third method to alter strains is genetic engineering, which has been demonstrated in many successful examples, and which is horizontal gene transfer via a vector. Researchers must know which genes need to be transferred in order to express the desired phenotype. Genetic engineering requires extensive metabolic knowledge, which is often limited by invalid assumptions. Most methodologies require a constructed plasmid containing the excised exogenous gene of interest along with an origin of replication and an appropriate promoter. This plasmid is then cloned and must be inserted into the host species via transformation, transduction, or conjugation, or friction via the Yoshida Effect. Transposons have also been transferred from one species to another in vitro and may be spontaneously incorporated into the chromosomal DNA, but this technique also initially requires an artificial vector to initiate the transfer. Extensive, robust techniques are published for *E. coli* that result in negligible changes in the genetically modified organism (GMO) growth rate or metabolic function. However, other species are not so well understood and may display faulty gene expression of the inserted plasmid, resistance to the initial transformation, or lose the exogenous plasmid easily. Another major disadvantage is the classification of resulting strains as GMOs, which can limit or exclude some industrial applications.

There is a need for an alternative, non-GMO, economically viable method to perform horizontal gene transfer for the purpose of modifying industrial microbial strains.

BRIEF SUMMARY OF THE INVENTION

Methods for producing chimeric microbial hybrids, through horizontal gene transfer without the use of a vector, are provided herein. These methods use a series of environmental pressure and selection tools to perform directed evolution using natural conjugation, transformation, or another mechanism for gene transfer across microbial species. Many publications have used the genomic sequence data of naturally occurring organisms to support the hypothesis of lateral gene transfer between diverse species in nature, e.g., by transformation, transduction, conjugation, friction, or by some other gene transfer event. However, this phenomenon has not been reported to occur in a laboratory setting across disparate species without the use of a vector or bacteriophage. Although not wishing to be bound by theory, the methods disclosed herein demonstrate that gene transfer across diverse microbial species may be a last resort survival mechanism that engages when the environment reaches a level of stress such that replication is no longer possible.

The methods include using dual selective pressure that encourages gene transfer to occur via natural conjugation, transformation, or possibly another mechanism across disparate species without the addition of a vector. Additionally, the methods may or may not use a pre-stressor to engage gene expression to promote gene transfer. Microbial cells that are selected in accordance with the methods are described herein.

In one aspect, a method is provided for creating chimeric microbial hybrids. The method includes pairing two different strains or species where the parental donor expresses a phenotype or contains genes of interest to transfer to the parental host. Parents, in separate cultures, may be placed under an additional, pre-determined environmental stressor prior to combining them together in one culture. Following this optional stressor, parents are then placed together in a liquid culture and then concentrated. Concentration can be done by natural settling, desiccation, lyophilization, evaporation, centrifugation or passing cells through a filter. Filters and/or concentrated cells are then put on selective pressure plates or liquid containing an exclusive environmental stressor for each strain or species. In some embodiments, these stressors are separate and complimentary for each parent strain. In some embodiments, the appropriate stressor is part of the incubation environment instead of the medium. Each stressor is added at a concentration or level sufficient to cause the microbial strain reproduction and growth to cease, for example, by at least about 95% to about 100%. Microbial colonies are selected by assessing the phenotype of said colonies. In some embodiments, resulting chimeras are genetic hybrids of both parents and express a new phenotype in response to the host's environmental stressor in the selective medium or surrounding environment. Strains resulting from this process are referred to herein as "chimeras" or "microbial hybrids."

In some embodiments, a method for chromosomal, horizontal gene transfer between two different microbial parent strains is provided to transfer genetic material between the microbial strains, without the use of a vector or other genetic engineering, molecular cloning, or recombinant DNA technology to transfer DNA that has been first removed from an organism prior to transfer to another organism. The method includes combining cells of first and second microbial parent strains together onto a solid growth medium or into a liquid growth medium. The growth medium and/or the environment surrounding or in contact with the growth medium includes at least one separate stressor for each of the parent strains, and a microbial hybrid strain is produced that is a genetic hybrid of the first and second parent strains and that expresses at least one phenotypic trait from genetic material that has been transferred from the first parent strain to the second parent strain. In some embodiments, the microbial hybrid expresses phenotypic traits from genetic material contributed from both parent strains.

Microbial hybrids may be produced with various desirable properties. In some embodiments, the microbial hybrid is biotherapeutic for one or more disease condition(s), i.e., may be used as a biotherapeutic or in a biotherapeutic composition or formulation in a method for treatment of one or more disease condition(s). In some embodiments, the microbial hybrid has increased or decreased fitness for one or more industrial application(s), in comparison to the microbial parent strains from which it was derived. In some embodiments, the microbial hybrid strain produces one or more new commodity, in comparison to the microbial parent strains from which it was derived. In some embodiments, the microbial hybrid strain has probiotic properties, i.e., may be used as a probiotic or in a probiotic composition or formulation.

The microbial parent strains may be bacterial or fungal. In some embodiments, the first and second parent strains are different microbial species. In some embodiments, the first and second parent strains are different strains of the same species.

In some embodiments, at least one or both of the first and second microbial parent(s) is generally recognized as safe (GRAS). In some embodiments, the microbial hybrid is GRAS.

In some embodiments, the microbial hybrid contains DNA from one or both parent strain(s) of bacterial species selected from the genera *Lactobacillus, Bifidobacterium, Streptococcus, Clostridium, Mycoplasma, Bacillus, Staphylococcus, Lactococcus, Leuconostoc, Pediococcus, Enterococcus, Enterobacteriaceae, Escherichia, Pseudomonas, Bacteriodetes*, and *Actinobacteria*. In some embodiments, the microbial hybrid genotypes as a bacterial species selected from the genera *Lactobacillus, Bifidobacterium, Streptococcus, Clostridium, Mycoplasma, Bacillus, Staphylococcus, Lactococcus, Leuconostoc, Pediococcus, Enterococcus, Enterobacteriaceae, Escherichia, Pseudomonas, Bacteriodetes*, and *Actinobacteria*.

In some embodiments, the microbial hybrid contains DNA from one or both parent strain(s) of *Lactobacillus* species and/or genotypes as a *Lactobacillus* species, for example, selected from *Lactobacillus plantarum, Lactobacillus delbrueckii, Lactobacillus acidophilus, Lactobacillus brevis, Lactobacillus casei, Lactobacillus paracasei, Lactobacillus sanfransciscensis, Lactobacillus rhamnosus, Lactobacillus helveticus, Lactobacillus curvatus, Lactobacillus sakei, Lactobacillus buchneri, Lactobacillus fermentum*, and *Lactobacillus reuteri*.

In some embodiments, the microbial hybrid contains DNA from one or both parent strain(s) of *Bifidobacterium* species and/or genotypes as a *Bifidobacterium* species, for example, selected from *Bifidobacterium animalis, Bifidobacterium asteroids, Bifidobacterium bifidum, Bifidobacterium breve, Bifidobacterium denticum, Bifidobacterium faecale, Bifidobacterium infantis, Bifidobacterium longum, Bifidobacterium merycicum, Bifidobacterium ruminantium, Bifidobacterium thermacidophilum*, and *Bifidobacterium tsurumiense*.

In some embodiments, the microbial hybrid contains DNA from one or both parent strain(s) of fungal species selected from the genera *Saccharomyces, Schizosaccharomyces, Schefferomyces, Zygosaccharomyces, Yarrowia, Pichia, Dekkera, Klyveromyces, Candida, Metschnikowia*, and *Torulaspora*. In some embodiments, the microbial hybrid genotypes as a fungal species selected from the genera *Saccharomyces, Schizosaccharomyces, Schefferomyces, Zygosaccharomyces, Yarrowia, Pichia, Dekkera, Klyveromyces, Candida, Metschnikowia*, and *Torulaspora*.

In some embodiments, the microbial hybrid contains DNA from one or both parent strain(s) of *Saccharomyces* species and/or genotypes as a *Saccharomyces* species, for example, selected from *Saccharomyces cerevisiae* var. *boulardii, Saccharomyces cerevisiae, Saccharomyces pastorianus, Saccharomyces fragilis*, and *Saccharomyces bayanus*.

In some embodiments, each of the stressors is present at a concentration that is sufficient to inhibit growth of the microbial parent that is sensitive to the stressor by about at least about 80% to about 100%, or any of at least about 80%, 85%, 90%, 95%, 98%, 99%, or 100%, or any of about 85%, 90%, 95%, 98%, or 99%, to 100%.

In one embodiment, the environmental stressor is an antibiotic or antifungal substance. In one embodiment, antibiotic or antifungal substance is included in the growth medium at a concentration of about 1 µg/ml to about 1 mg/ml.

In one embodiment, the environmental stressor is an organic compound, for example, an organic compound found in plant oil. In one embodiment, the organic compound added to the growth medium is at a concentration from about 1 pg/ml to about 1 g/ml.

In one embodiment, the environmental stressor is a solvent. In one embodiment, the solvent is added to the growth medium in a concentration from about 1 pg/ml to about 1 g/ml.

In one embodiment, the environmental stressor is high temperature. In one embodiment, the atmospheric temperature is about 21° C. to about 130° C.

In one embodiment, the environmental stressor is low temperature. In one embodiment, the atmospheric temperature is about −200° C. to about 21° C.

In one embodiment, the environmental stressor is ultraviolet light. In one embodiment, the ultraviolet light duration is at least about half a second and no longer than two seconds.

In one embodiment, the environmental stressor is osmotic. In one embodiment the osmotic stressor added to the growth medium is a sugar such as glucose at a concentration of about 5 mM to about 10 M.

In one embodiment, the environmental stressor is an inorganic chemical. In one embodiment, the inorganic chemical added to the growth medium is at a concentration of at least about 1 pg/ml.

In one embodiment, the environmental stressor is ionizing radiation. In one embodiment, cultures are subjected to as low as about 1 Gy/min to as high as about 250 Gy/min of ionizing radiation.

In one embodiment, the environmental stressor is the composition of atmospheric gas. In one embodiment, oxygen ($O_2$) is added to the atmosphere, e.g., to an anaerobic atmosphere, at a concentration of at least about 0.2% v/v. In another embodiment, the atmospheric oxygen is limited to a concentration of 0% or substantially 0% v/v.

In one embodiment, the environmental stressor is a vitamin or co-factor, or lack thereof. In some embodiments, the vitamin or co-factor is not included in the growth medium (0%) or is limited to a very low level (substantially 0% w/w). In one embodiment, vitamin or co-factor is biotin, for example, at a concentration of 0% or limited to substantially 0% w/w.

In one embodiment, the environmental stressor is an acid used to lower the pH. In one embodiment, the amount of added acid is at a concentration of about 0.1 mM to about 10 M.

In one embodiment, the environmental stressor is a base used to increase the pH. In one embodiment, the amount of added base is at a concentration of about 0.1 mM to about 10 M.

In one embodiment, the environmental stressor is the carbohydrate source. In one embodiment, the amount of carbohydrate source that the parent can metabolize for growth in the growth medium is limited to a concentration of 0% or substantially 0% w/w.

In one embodiment, the environmental stressor is the nitrogen source. In some embodiments, the nitrogen source is not included in the growth medium (0%) or is limited to a very low level (substantially 0% w/w). In one embodiment, the nitrogen source is one or more amino acid(s) or protein(s) in the growth medium, for example, at a concentration of 0% or limited to substantially 0% w/w.

In one embodiment, the environmental stressor is a biological toxin. In one embodiment, the toxin is included in the growth medium at a concentration from about 100 pg/ml to about 1 g/ml.

In one embodiment, the environmental stressor is a peptide, for example, a microbial peptide. In one embodiment, the peptide is included in the growth medium at a concentration of about 10 mg/kg to about 1 g/kg.

In one embodiment, the environmental stressor is a preservative substance, e.g., a food preservative substance. In one embodiment, the preservative substance is included in the growth medium at a concentration of about 0.5 mM to about 1 M.

In one embodiment, the environmental stressor is an herbicide. In one embodiment, the herbicide is included in the growth medium at a concentration of about 1 pg/kg to about 1 g/kg.

In one embodiment, the environmental stressor is a fungicide or bacteriocide. In one embodiment, the fungicide or bacteriocide is included in the growth medium at a concentration of about 1 pg/kg to about 1 g/kg.

In one embodiment, the environmental stressor is a pesticide. In one embodiment, the pesticide is included in the growth medium at a concentration between 1 pg/kg and 1 g/kg.

In one embodiment, the environmental stressor is a filtrate of another microbe's spent fermentation broth. For example, in one embodiment, filtered spent broth from a *Clostridium difficile* fermentation is used as a stressor. In one embodiment, the filtered spent broth is added to the growth medium at a concentration of about 1% to about 90% v/v.

The microbial parental strains may be bacterial or fungal. In some embodiments, the parental strains are not classified in the same kingdom. In one embodiment, the parental strains are not classified in the same phylum.

In some embodiments, both the intended host and donor strains have different environmental stressors applied in tandem.

In some embodiments, the pre-stressor applied is of a different variety from the selective environment of the gene transfer.

In some embodiments, the parent intended to be the donor strain can become the host.

In some embodiments, any of the environmental stressors described above may be used as a secondary stressor after gene transfer has taken place on a primary stressor, to narrow or specialize strain selection.

Some embodiments result in microbial hybrids that retain some genes from both parents.

Some embodiments result in microbial hybrids that are polyploidal, meaning they retain the entire genomes from both parents.

Microbial hybrids produced by the methods described herein have undergone horizontal gene transfer without the use of a vector.

Microbial hybrids are considered to be chimeras, and these terms are used interchangeably herein.

In some embodiments, the resulting microbial hybrids (from a single colony) may display multiple phenotypes depending on the environment in which they are grown.

The method for producing chimeric microbial hybrids may include: (a) applying a pre-stressor to each separate parental strain sufficient to inhibit growth by at least about 10%, but not more than about 90%; (b) combining the two parents together in liquid medium and then concentrating them together on a filter, e.g., a filter with a pore size small enough to concentrate the cells, e.g., a 0.2 μm filter; (c) placing the filter cell-side down onto a dual selection plate, or placing the filter in dual selection liquid medium, wherein the dual selection plate or liquid medium contains an amount of one or more environmental stressor(s) sufficient to inhibit growth of both strains by about 100%; (d) removing the filter from the first dual selection plate (gene transfer plate) or from dual selection liquid medium, vortexing and centrifuging the filter in liquid and resuspending and plating each pellet on a second dual selection plate; (e) selecting colonies that grow on the second dual selection plates. Optionally, the resulting the resulting microbial hybrids may be assessed for chimeric traits. In one embodiment, the method further includes: (f) restreaking the colonies from the second selection plates in (e) on to a third set of selection plates that contain solid medium with about the same amount of environmental stressor(s) as used in step (c); (g) incubating the third selection plates under conditions suitable for growth of bacterial colonies; (h) repeating steps (f) and (g); and (i) selecting colonies that grow on the fourth and final selection plates; (j) optionally, applying a stressor as a secondary selection to narrow results or assess for the transfer of a secondary phenotype; and (k) optionally, assessing the resulting microbial hybrids for chimeric phenotypes and/or genotypes.

The resulting microbial hybrids may be used as new parental host or donor strains to use this method for further strain alteration.

Microbial hybrid strains are provided, produced in accordance with the methods disclosed herein, e.g., non-naturally occurring microbial hybrids that are derived from two different microbial strains or species without the use of recombinant DNA technology or introduction of DNA via a vector or introduction of DNA via other technologies for introducing exogenous DNA that has been removed from the organism from which it is derived prior to transfer into a cell. In various embodiments, the microbial hybrid strains may have useful and/or desirable properties including, but not limited to, biotherapeutic activity, probiotic activity, and/or ability to produce a commodity of interest.

Methods of producing compounds of interest, such as a commodity compound, are provided, including culturing a microbial hybrid produced in accordance with the methods as described herein in a growth medium under conditions suitable for growth of the hybrid and production of the compound or commodity of interest, and optionally recovering the compound or commodity from the growth medium.

Method of treating an individual with a condition that is treatable with a biotherapeutic or probiotic are also provided, including administering an effective amount of a microbial hybrid with biotherapeutic or probiotic activity produced in accordance with a method as described herein to an individual in need thereof, wherein a condition of the individual that responds to the biotherapeutic or probiotic activity is alleviated, ameliorated, reduced, or eliminated.

BRIEF DESCRIPTION OF THE DRAWINGS

FIGS. 1A-1E display the hybrid nature of the chimeric microbial hybrids, showing growth after an anaerobic incubation at 37° C. for 72 hours. Plates contained minimal medium as described in Example 2. Color change from purple to yellow indicates acid production and growth (Note: pictures are gray scale). The parental donor in FIG. 1A is *Clostridium beijerinckii* and shows robust growth reflecting its protrophic ability to make essential amino acids not present in the medium. The parental host, *Lactobacillus plantarum*, in FIG. 1B, does not grow at all due to its inherent amino acid auxotrophies. Three of ten chimeric strains are shown in FIGS. 1C, 1D, and 1E; these represent the variety of growth seen among the microbial hybrids. FIG. 1C is chimera C-1, FIG. 1D is chimera C-8, and FIG. 1E is chimera C-9. The arrow in FIG. 1D is there to point out the single yellow colony growing at the top of the plate.

FIGS. 2A-2E show growth after aerobic incubation at 42° C. for 24 hours. Plates contained an enriched protein medium as described in Example 2. The parental donor in FIG. 2A is *Clostridium beijerinckii* and shows no growth reflecting its inability to replicate at 42° C. in the presence of oxygen. The parental host, *Lactobacillus plantarum*, in FIG. 2B, shows robust growth in oxygen at 42° C. Three of ten chimeric strains are shown in FIGS. 2C, 2D, and 2E, which represent the variety of growth seen among the microbial hybrids; they are the same chimeras pictured in FIGS. 1C, 1D, and 1E. FIG. 2C is chimera C-1, FIG. 2D is chimera C-8, and FIG. 2E is chimera C-9. The arrow in FIG. 2E is there to point out the single colonies growing at the top of the plate. Neither parent showed growth on its own under the combined conditions of FIGS. 1A-1E and FIGS. 2A-2E. However, all ten resulting chimeric strains are able to grow on minimal medium at 42° C. aerobically.

FIGS. 3A, 3B, and 3C display the results of Biomerieux's CH50 tests done anaerobically for 48 hours at 35° C. Carbohydrate metabolism was tested anaerobically for 48 different carbon sources. The boxes shaded in dark grey represent carbohydrate metabolism functionality that was shared between the two parents before the gene transfer. Light grey traits are those unique to the *Clostridium* parent (P-C.b.). Black traits are those unique to the *Lactobacillus* parent (P-L.p.). Traits that are colored in each row represent a positive result for the metabolism of that column's carbon source. Note that all of the chimeric strains (C-1: C-10) have a combination of abilities when compared to the parental strains. The white-shaded trait, potassium gluconate metabolism, is more difficult to explain. This is a carbon source which nine out of ten chimeras are able to metabolize, unlike both of their parents. It is possible, although not wishing to be bound by theory, that both parent strains possess nonfunctional copies of this gene which has been rendered functional with both copies present.

FIGS. 4A-4D show chimeric testing to determine the antibiotic susceptibility of six different antibiotics. Starting at the 12:00 position at the top of the plate and moving clockwise around the plate, these antibiotics are: amoxicillin/clavulinic acid (20 μg/10 μg), azithromycin (15 μg), carbenicillin (5 μg), ciprofloxin (5 μg), metronidazole (5 μg), and vancomycin (30 μg). The *Clostridium* parent is pictured in FIG. 4A and is susceptible to all six antibiotics. The *Lactobacillus* parent, shown in FIG. 4B, shows some clearing around amoxicillin/clavulinic acid although it is considered to be resistant based on standard susceptibility charts. The *Lactobacillus* parent is susceptible to azithromycin. The carbenicillin zone of clearance is considered "resistant" according to standard susceptibility charts. All of the chimeras, represented by C-7 in FIG. 4D, with the exception of C-1, retained similar susceptibilities and resistances as the *Lactobacillus* parent. C-1, shown in FIG. 4C, has antibiotic susceptibility closer to the *Clostridium* parent as it is susceptible to 5/6 antibiotics, with metronidazole resistance being expressed as a new trait.

FIG. 5 shows growth of the chimeras in comparison to the parents in a diluted, modified BHI medium. All strains show increased growth at diluted concentrations of media compared to the parent, Lactobacillus amino acid auxotroph, P-L.p., and commercially available Lactobacillus, 299v. Growth was in an anaerobic chamber at 35° C. for 48 hours. C-1 showed lower growth than expected as it prefers to grow at 42° C. It is suspected that growth would be improved at higher temperatures. 35° C. was chosen to assure the growth of the Clostridium parent. C. beijerinckii, P-C.b., has a slow growth rate and as such, concentrations of BHI at 1.4% w/w and 2.8% w/w did not show detectable growth until 72 hours (data not shown).

FIG. 8 shows four micrographs (100× objective) taken of single colonies from plates grown in the same conditions. Growth was on modified BHI plates grown anaerobically for 7 days at 37° C. FIG. 8A is a micrograph of the parent, Lactobacillus plantarum. FIG. 8B is a micrograph of the Clostridium parent; it is littered with spores and debris from lysed endospores. FIG. 8C is a micrograph of chimera C-9 which is capable of producing colonies with morphological phenotypes of both FIGS. 8C and 8D. FIG. 8C shows colonies growing close together, whereas the colonies in FIG. 8D are far apart. The colonies in FIG. 8D, when moved to aerobic conditions, especially on minimal medium, will become oligo-sporogenic as seen in FIG. 7.

FIGS. 9A and 9B contains two micrographs of Saccharomyces cerevisiae var. boulardii, seen budding in a rich medium (FIG. 9A) versus the physical attachment seen during horizontal gene transfer (using the method described herein) in a stressful medium (FIG. 9B). Yeast which are exchanging genes are unable to bud, but are able to use this gene transfer method as a last resort for survival. Similar observations have been made in the bacterial cultures where strains are unable to divide, but are still able to exchange DNA in stressful conditions (micrographs not shown).

FIGS. 10A and 10B show the results of 72-hour growth at 30-31° C. using Biomerieux's 20 C Aux yeast identification kit. Carbohydrate metabolism was tested aerobically for 20 different carbon sources. The boxes shaded in grey represent carbohydrate metabolism functionality that was shared between the two parents before the gene transfer method was applied. White traits are those unique to the Metschnikowia parent. Black traits are those unique to the Saccharomyces parent. Traits that are marked "+" in each row represent a positive result for the metabolism of that column's carbon source; "++" indicated excessive growth. Note that all of the chimeric strains (YC-1: YC-11) have a combination of abilities when compared to the parental strains.

FIGS. 12A, 12B, and 12C show Biomerieux api 50 CH results for both parents, as compared to the resulting chimeric microbial hybrids. The parental host Bifidobacterium faecale can metabolize just 12 carbon sources, as detected by this assay, whereas the resulting chimeras (C-5, C-7, and C-9) can metabolize up to 18 carbon sources. Although the stressor for Bifidobacterium during the gene transfer method was a lack of amino acids in the medium, additional traits such as the ability to metabolize these 6 additional carbon sources were laterally transferred at the same time as amino acid synthesis genes were added.

FIG. 13 shows growth of a chimeric Bifidobacterium faecale strain, C-5, in comparison to its gram negative donor parent, P-1 (Grimontella senegalensis) and its gram positive host parent, P-2 (Bifidobacterium faecale). Five milliliter aliquots of M9 raffinose medium containing bromocresol purple were inoculated with a single colony from a BHI plate. Cultures were incubated for 48 hours at 37° C. in an anaerobic chamber. Growth was only detected in the C-5 cultures, as seen by the lighter color of the media due to acid production. Neither wild-type parent grew in the medium as P-1 cannot utilize raffinose as a carbon source and P-2 cannot grow without protein or amino acids present.

DETAILED DESCRIPTION

Figure 6:
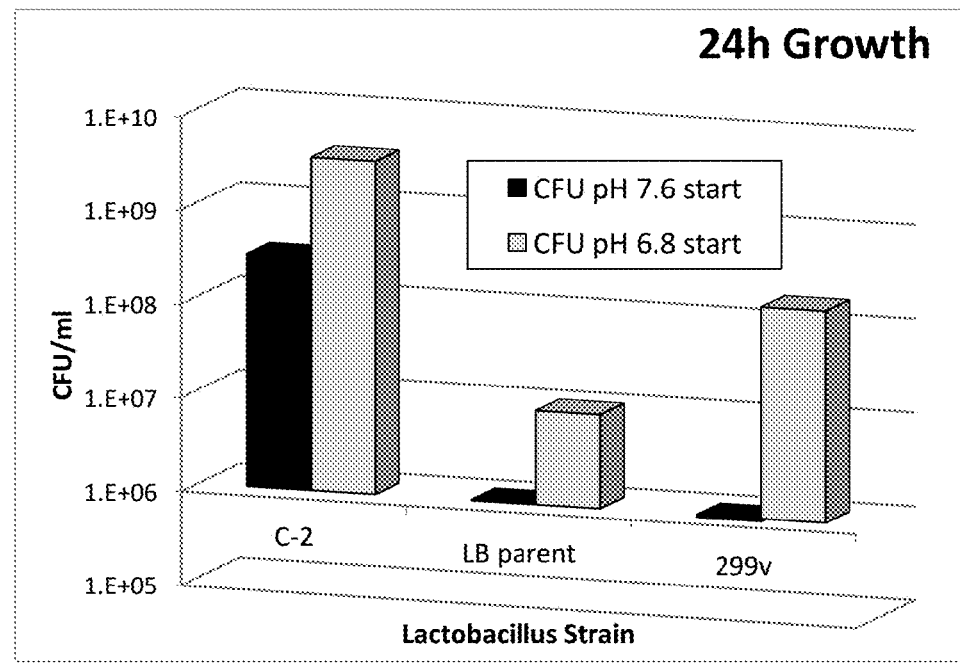
FIG. 6 shows growth of Lactobacillus chimera C-2 compared to its Lactobacillus parent and commercially available Lactobacillus 299v. both the "pH 7.6 start" and "pH 6.8 start" medium had approximately 0.5 gram of glucose derived from a medium containing 20% brain heart infusion (BHI) agar and 1 g/L yeast extract with 12 g/L additional sugar (all glucose in pH 7.6, colonic sugars in pH 6.8). CFUs tend to be equivalent in both sugar types limited by final pH. Lactobacillus in general have a difficult time starting at a pH greater than 7. The large intestine of humans has a pH range from 8.0 (following the small intestine) to 5.0. The Lactobacillus chimera (C-2) should be able to start growing sooner in the caecum of a human's large intestine, in comparison with its parent (299v), as it has the ability to start growing at a higher pH. Media was inoculated form overnight cultures at 1×10$^6$ CFU/ml and incubated for 24 hours inside an anaerobic chamber kept at 37° C.

The invention provides methods for producing chimeric microbial hybrids.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

Numeric ranges provided herein are inclusive of the numbers defining the range.

Definitions

A "chimeric organism" or "chimera" refers to a single-celled organism that contains functional genes from two or more microbial species.

A "microbe" or "microbial strain" refers to a single-celled organism such as a bacterium or fungal cell, for example, yeast.

The term "recombination" is the process or act of exchanges of genes between chromosomes, resulting in a different genetic combination and ultimately in the formation of unique offspring with chromosomes that are different from those in the parents.

"Conjugation" is the transfer of genetic material between microbes by direct cell-to-cell contact or by a bridge-like connection between two cells.

"Hybrid" is an organism bred from two genetically distinct varieties, species, or genera.

"Genetic engineering" is the science of altering and cloning genes to produce a new trait in an organism or to make a biological substance, such as a protein or hormone.

"Phenotype" is the observable characteristics of an organism, dependent upon genotype and environment.

"Genotype" is the genetic constitution of an organism.

"Horizontal gene transfer," also referred to as "gene transfer" herein, is the transmission of DNA between different species' genomes.

A "vector" is a DNA molecule used as a vehicle to artificially carry foreign genetic material from one cell into another cell, where it can be replicated and/or expressed. A vector containing foreign DNA is termed recombinant DNA. Examples include plasmids and transposons.

"Recombinant DNA (rDNA) molecules" are DNA molecules formed by laboratory methods of genetic recombination (such as molecular cloning) to bring together genetic material from multiple sources, creating sequences that would not otherwise be found in the genome.

"Strain alteration" is the addition or deletion of DNA through natural or artificial means to change gene expression in a species.

"Mutagenesis" is the act of changing the nucleotide sequence through exposure to mutagens.

A "mutagen" is a biological, chemical, or physical agent, process, or substance that causes permanent genetic change (mutation) in a cell (other than which occurs during normal cell growth) due to genetic alterations or loss of genes or chromosomes.

A "protoplast" is a living plant, bacterial, or fungal cell that has had its cell wall completely or partially removed using either mechanical, chemical, or enzymatic means.

A "plasmid" is an extra-chromosomal genetic element found among various strains of bacteria.

"Transformation" the transfer of genetic information between microbes by means of histone-free intracellular DNA fragments derived from bacterial donor cells and incorporated into a competent recipient cell.

"Transduction" refers to the insertion of DNA via a bacteriophage into a bacterial cell or via a virus into a eukaryotic cell.

"Eukaryotic cells" are cells of higher organisms or fungi, such as yeast, that contain a nucleus surrounded by a membrane and whose DNA is bound together by proteins (histones) into chromosomes. The cells of eukaryotes also contain intracellular compartments, such as endoplasmic reticulum and numerous specialized organelles that are not found in prokaryotic cells, such as mitochondria, Golgi bodies, and lysosomes.

"Prokaryotic cells" are cells of organisms, such as bacteria, that do not have a true nucleus.

A "transposon" is a chromosomal segment that can undergo transposition, especially a segment of bacterial DNA that can be translocated as a whole between chromosomal, phage, and plasmid DNA in the absence of a complementary sequence in the host DNA.

The "Yoshida Effect" is a method of plasmid transfer involving cell wall friction which can be done artificially or can occur naturally during a friction event such as an earthquake.

A "GMO" (as defined in the United States) is a genetically modified organism developed through genetic engineering.

An "environmental stressor" is a factor in a cell's surroundings that threatens homeostasis.

"Homeostasis" is the tendency toward a relatively stable equilibrium between interdependent elements, especially as maintained by physiological processes.

A "prototroph" is an organism or cell capable of synthesizing a required nutrient. For example, a prototroph may auto-synthesize essential amino acids.

An "auxotroph" is an organism or cell that is incapable of producing a nutrient required for growth. For example, an auxotroph may be incapable of producing one or more essential amino acid(s).

An "organic compound" is any member of a large class of gaseous, liquid, or solid chemical compounds whose molecules contain carbon and hydrogen.

An "osmotic stressor" is a factor in the environment that causes a change in the solute concentration around a cell, causing a rapid change in the movement of water across its cell membrane.

A "cofactor" is a non-protein chemical compound that is required for a protein's biological activity. These proteins are commonly enzymes, and cofactors can be considered "helper molecules" that assist in biochemical transformations.

The "parental donor" is the microbial strain providing the desired phenotype to be transferred to another species or strain via a gene transfer method as described herein.

The "parental host" is the microbial strain receiving exogenous DNA from another species or strain via a gene transfer method as described herein.

"Polyploidy" is a condition in which an organism acquires one or more additional set(s) of chromosome(s).

"Phenotypic plasticity" is the ability of one genotype to produce more than one phenotype when exposed to different environments, e.g., the ability of an organism to change its phenotype in response to changes in the environment.

"Wild-type" refers to a microorganism as it occurs in nature.

"Parent strain" refers to a microbial strain from which a chimera is derived.

The term "culturing" refers to growing a population of cells, e.g., microbial cells, under suitable conditions for growth, in a liquid or solid medium.

The term "derived from" generally indicates that one specified material finds its origin in another specified material or has features that can be described with reference to another specified material.

"Oligo-sporogenic" is a microbial strain in which only a few members of the colony form spores.

The abbreviation "MIC" refers to minimum inhibitory concentration.

The abbreviation "CFU" refers to colony forming unit.

"Budding" is a form of asexual reproduction, for example, in yeast, in which new individuals form from outgrowths ("buds") on the bodies of mature organisms. These outgrowths grow by means of mitotic cell division.

"Toxin A" is an enterotoxin produced by pathogenic strains of *Clostridium difficile*. This virulent toxin acts by modifying eukaryotic host cells' GTPase enzymes by glucosylation, leading to changes in cellular activities.

"Toxin B" is a cytotoxin that is produced by pathogenic strains of *Clostridium difficile*. This virulent toxin acts to target eukaryotic cells, disturbing signal transduction mechanisms, which leads to dysfunctioning of cell structure, cell-cell junctions, and cell lysis.

"Spent fermentation broth" refers to the supernatant of a microbial culture that has ceased growing.

The abbreviation "GRAS" refers to "generally recognized as safe," a category created by the FDA to describe substances allowed in food products.

A "solvent" refers to a liquid or gas that is capable of dissolving a solid or another liquid or gas. Although not wishing to be bound by theory, a solvent may act as a microbial stressor by affecting the maintenance of the cellular membrane fluidity and lipid-phase stability.

"A," "an" and "the" include plural references unless the context clearly dictates otherwise.

Methods for Producing Chimeric Microbial Hybrids

Methods are provided for producing a chimeric microbial hybrid. Some or all of the following steps may be performed:

(1) Two microbial strains or species are chosen; one is the desired parental host and the other is the desired parental donor. An appropriate parental host expresses a final desired phenotype, for example a morphological phenotype, of the resulting chimeric hybrid strain, while the parental donor is a strain that expresses a phenotypic trait that is desired in the host which the host does not currently express. In one embodiment, the strains may be classified in different kingdoms. In another embodiment, the strains may be classified in different phyla. In addition, the parental donor must also lack a phenotype which is expressed in the parental host. Both of these unique phenotypes, one in the donor, and one in the host, must have at least one corresponding environmental stressor that can either be incorporated into the process medium or into the surrounding environment.

(2) To provide efficacy, it is often necessary to perform a minimum inhibitory concentration (MIC) test to determine the highest (or lowest) amount of a selected condition that each parental species can survive to form single colonies on a solid or liquid medium. The MIC will also provide the amount of environmental stressor that allows for no colony forming units (CFUs) to grow in the same conditions for the other parent.

(3) Once MIC information is obtained (e.g., either determined in (2) or already known), plates with solid medium or liquid medium may be made containing both stressors, e.g., a stressor for each of the two microbial strains. Alternatively, one or both of the stressors may be contained in the surrounding environment in which the gene transfer method is performed instead of the medium (e.g. percentage of atmospheric gases or incubation temperature). Cells of interest may be grown to a density of about $1\times10^8$/ml for the parental donor and to about 2-$3\times10^8$/ml for the parental host. For some time period before, for example, at least a half hour before starting the gene transfer method, less severe environmental pre-stressors may be applied to which both strains are susceptible. Alternatively, different stressors to which each strain individually is susceptible may be applied prior to starting the gene transfer method. In some embodiments, it is important or desirable that these pre-stressors be applied to increase gene transfer, but it is not necessary in order to have a successful chimeric result. Pre-stressors are typically applied before combining the two parental strains together. In order to determine these pre-stressors, which help to prime the parents for gene transfer, an MIC is advised. A milder concentration may be used that is well under the MIC, but results in some cell mortality.

(4) Following pre-stressor incubation, if applicable, or as the initial step in production of a chimeric microbial hybrid, cells from each parent, for example logarithmic phase cells, e.g., mid- to late log phase, are combined together and concentrated, for example, by desiccation, lyophilization, evaporation, filtration, centrifugation, or settling.

In one embodiment, the filter and/or cell pellet is then washed, for example, with phosphate buffered saline (PBS). In one embodiment, 5 ml of cells from each parent are combined together for a total of 10 ml and concentrated by filtration, for example, on to a 0.2 μm filter, followed by washing of the filter with a solution appropriate to maintain integrity of the cells, such as PBS. In one embodiment, the filter is washed with 10 ml of PBS. This gene transfer filter and/or concentrated cells are then either placed face down on solid, dual selection medium, e.g., determined in (1) and referenced in (2) above, or placed in a tube, e.g., a conical tube until just covered in a liquid, dual selection medium. Gene transfer filters are then incubated, under the appropriately selected conditions, for some period of time, for example, 48 hours.

In one embodiment, cells are concentrated by centrifugation, washed twice with PBS and then placed in a small volume of liquid containing dual stressors. Liquid gene transfer cultures are then incubated under the appropriately selected conditions, for some period of time, for example 48 hours.

In one embodiment, cells are concentrated by desiccation or lyophilization. These dried cells are then added to a small volume of liquid containing dual stressors. Liquid gene transfer cultures are then incubated under the appropriately selected conditions, for some period of time, for example 48 hours.

(5) Post incubation, the gene transfer filter from solid medium, or concentrated liquid culture, is placed into a sterile tube, e.g., a microcentrifuge tube, with an appropriate amount of liquid solution, e.g., 1 ml of PBS. In addition, any visible biofilm may be scraped off of the gene transfer plate and placed inside the same tube, e.g., microcentrifuge tube. For both solid and liquid medium filter incubation, the tubes containing the filters and/or liquid containing concentrated cells are agitated, e.g., vortexed and then the cells are separated from liquid, e.g., spun down in a centrifuge, e.g., at 8000RCF for ten minutes. An amount of supernatant is removed, e.g., 800 μl. The cell pellet with the remaining supernatant, e.g., 200 μl, is resuspended and plated onto a selective medium. The supernatant is removed, and the cell pellet is resuspended in an appropriate volume of solution, e.g., 200 μl of PBS, and then plated onto selective medium, e.g., a solid or semi-solid medium that contains the desired selection agent(s) and/or in environmental selection condition(s). The plates are incubated in desired conditions for up to five days to determine CFUs. Typically, colonies may appear as early as 12 hours post-plating, but can take up to five days to grow.

In one embodiment, resulting cells that have been separated from liquid can be placed in a continuous reactor (instead of plating) in order to select chimeras for desired traits. In one embodiment, dual stressors can be added at increasing amounts until only one strain remains. In one embodiment, dilution rates can be increased to isolate the fastest growing chimera.

(6) There may be false positives that form CFUs as some strains will grow together commensally and/or live off the detritus provided from cell debris on the plate. In addition, it has been observed that some strains will express adaptations that will not transfer chromosomally to the next generation via single colony transfer. In order to rule false positives out, all CFUs may be re-streaked to a single colony onto a new selection plate. In some embodiments, a dual re-streak, one onto selective medium and one onto rich medium, is preferable, as there are some cases where it is too stressful for microbial hybrids to initially transfer from selective medium back to selective medium. In addition, colonies may not survive long enough to transfer them from the selective medium before dying. If colonies appear on rich medium, but not the selective medium, an additional single colony transfer from rich to dual selective medium is performed to determine if the phenotype is still present. The new microbial hybrid strain must also retain its new phenotype post storage (e.g., cryogenic or sporulation from a single colony) to rule out temporary, epigenetic adaptations. Either parental strain can become the host or donor. Therefore, the morphology of the new hybrids is noted. Typically, the microbial hybrid will type (e.g., 16S rRNA) as the main morphological phenotype it expresses.

(7) As an optional step, resulting microbial hybrids may be streaked onto an additional plate that contains or is in the presence of a stressor that is difficult to use as the primary stressor, for example, because it has no MIC, yet resistance to the substance or condition is still desired. This step may also be used to make sure desired phenotype(s) of the original parental host have been retained.

(8) The chimeric microbial hybrid strains are assessed via phenotype tests and/or genotype tests to determine which phenotypes and/or genes have been transferred to the parental host. Successful chimeric microbial hybrids will have traits and genes from both parents.

In one embodiment, the environmental stressor is an antibiotic or antifungal substance. In one embodiment, antibiotic or antifungal substance is included in the growth medium at concentration of about 1 μg/ml to about 1 mg/ml. In some embodiments, the antibiotic or antifungal substance is included in the growth medium at a concentration of any of at least about 1 μg/ml, 10 μg/ml, 50 μg/ml, 100 μg/ml, 250 μg/ml, 500 μg/ml, 600 μg/ml, 700 μg/ml, 800 μg/ml, 900 μg/ml, or 950 μg/ml, or any of about 1 μg/ml to about 10 μg/ml, about 5 μg/ml to about 25 μg/ml, about 10 μg/ml to about 50 μg/ml, about 25 μg/ml to about 75 μg/ml, about 50 μg/ml to about 100 μg/ml, about 75 μg/ml to about 200 μg/ml, about 100 μg/ml to about 250 μg/ml, about 150 μg/ml to about 300 μg/ml, about 250 μg/ml to about 500 μg/ml, about 350 μg/ml to about 600 μg/ml, about 500 μg/ml to about 750 μg/ml, about 600 μg/ml to about 900 μg/ml, about 750 μg/ml to about 1000 μg/ml, about 1 μg/ml to about 250 μg/ml, about 1 μg/ml to about 500 μg/ml, about 250 μg/ml to about 750 μg/ml, or about 500 μg/ml to about 1000 μg/ml. In various embodiments, the antibiotic substance falls into one of the following antibiotic classes: aminoglycosides, ansamycins, carbapenems, cephalosporins, glycopeptides, lincosamides, macrolides, oxazolidinones, penicillins, polypeptides, quinolones, sulfonamides, or tetracyclines. In one embodiment, the aminoglycoside is gentamicin, kanamycin, or neomycin. In one embodiment, the ansamycin is rifaximin. In one embodiment, the carbapenem is ertapenem, imipenem, or meropenem. In one embodiment, the cephalosporin is cefadroxil, cefoxitin, cefoperazone, cefepime, or ceftobiprole. In one embodiment, the glycopeptide is vancomycin or teicoplanin. In one embodiment, the lincosamide is clindamycin or lincomycin. In one embodiment, the macrolide is azithromycin, clarithromycin, or erythromycin. In one embodiment, the oxazolidinone is linezolid. In one embodiment, the penicillin is penicillin G, amoxicillin, Augmentin, ampicillin, carbenicillin, or methicillin. In one embodiment, the polypeptide is bacitracin, colistin, or polymyxin B. In one embodiment, the quinolone is ciprofloxacin, levofloxacin, nalidixic acid, or norfloxacin. In one embodiment, the sulfonamide is mafenide or sulfadimethoxine. In one embodiment, the tetracycline is tetracycline or doxycycline. In one embodiment, the antibiotic is rifampicin, chloramphenicol, thiamphenicol, metronidazole, or mupirocin.

In one embodiment, the environmental stressor is an organic compound, for example, found in plant oils such as olive oil, cinnamon oil, peppermint oil, thyme oil, rosemary oil, clove oil, parrafinic oil, mint oil, or garlic oil. In one embodiment, the organic compound added to the growth medium is at a concentration of about 1 pg/ml to about 1 g/ml. In some embodiments, the organic compound is included in the growth medium at a concentration of any of at least about 1 pg/ml, 10 pg/ml, 50 pg/ml, 100 pg/ml, 500 pg/ml, 750 pg/ml, 1 ng/ml, 10 ng/ml, 50 ng/ml 100 ng/ml 500 ng/ml, 750 ng/ml, 1 μg/ml, 10 μg/ml, 50 μg/ml, 500 μg/ml, 750 μg/ml, 1 mg/ml, 10 mg/ml, 50 mg/ml, 100 mg/ml, 500 mg/ml, 750 mg/ml or 950 mg/ml, or any of about 1 pg/ml to about 500 pg/ml, about 250 pg/ml to about 750 pg/ml, about 500 pg/ml to about 1 ng/ml, about 750 pg/ml to about 250 ng/ml, about 1 ng/ml to about 500 ng/ml, about 250 ng/ml to about 750 ng/ml, about 500 ng/ml to about 1 μg/ml, about 250 μg/ml to about 750 μg/ml, or about 500 μg/ml to about 1 mg/ml, about 750 μg/ml to about 250 mg/ml, about 250 mg/ml to about 750 mg/ml about 500 mg/ml to about 1 g/ml, about 1 pg/ml to about 1 ng/ml, about 1 ng/ml to about 1 μg/ml, about 1 μg/ml to about 1 mg/ml, or about 1 mg/ml to about 1 g/ml. In some embodiments, the organic compound is a phenolic compound such as oleuropein. In some embodiments, the organic compound is a fatty acid, monoglyceride, or aldehyde.

In one embodiment, the environmental stressor is a solvent. In one embodiment, the solvent is added to the growth medium at a concentration of about 1 pg/ml to about 1 g/ml. In some embodiments, the solvent is included in the growth medium at a concentration of any of at least about 1 pg/ml, 10 pg/ml, 50 pg/ml, 100 pg/ml, 500 pg/ml, 750 pg/ml, 1 ng/ml, 10 ng/ml, 50 ng/ml 100 ng/ml 500 ng/ml, 750 ng/ml, 1 μg/ml, 10 μg/ml, 50 μg/ml, 500 μg/ml, 750 μg/ml, 1 mg/ml, 10 mg/ml, 50 mg/ml, 100 mg/ml, 500 mg/ml, 750 mg/ml or 950 mg/ml, or any of about 1 pg/ml to about 500 pg/ml, about 250 pg/ml to about 750 pg/ml, about 500 pg/ml to about 1 ng/ml, about 750 pg/ml to about 250 ng/ml, about 1 ng/ml to about 500 ng/ml, about 250 ng/ml to about 750 ng/ml, about 500 ng/ml to about 1 μg/ml, about 250 μg/ml to about 750 μg/ml, or about 500 μg/ml to about 1 mg/ml, about 750 μg/ml to about 250 mg/ml, about 250 mg/ml to about 750 mg/ml about 500 mg/ml to about 1 g/ml, about 1 pg/ml to about 1 ng/ml, about 1 ng/ml to about 1 μg/ml, about 1 μg/ml to about 1 mg/ml, or about 1 mg/ml to about 1 g/ml. In some embodiments, the solvent is acetic acid, acetone, acetonitrile, benzene, 1-butanol, 2-butanol, 2-butanone, t-butyl alcohol, carbon tetrachloride, chlorobenzene, chloroform, cyclohexane, decane, 1-2-dichloroethane, diethylene glycol, diethyl ether, diglyme, 1,2-dimethoxyethane (DME), dimethyl-formamide (DMF), dimethyl sulfoxide (DMSO), 1,4-dioxane, ethanol, ethyl acetate, ethylene glycol, glycerin, heptane, hexamethylphosphoramide (HMPA), Hexamethylphosphoroustriamide (HMPT), hexane, heptane, methanol, methyl t-butyl ether (MTBE), methylene chloride, N-methyl-2-pyrrolidinone (NMP), nitromethane, nonane, octane, pentane, ligroine, 1-propanol, 2-propanol, pyridine, tetrahydrofuran (THF), toluene, triethyl amine, o-xylene, m-xylene, orp-xylene.

In one embodiment, the environmental stressor is high temperature. In one embodiment, the atmospheric temperature is about 21° C. to about 130° C. In some embodiments, the atmospheric temperature is any of at least about 21° C., 25° C., 50° C., 75° C., 100° C., or 125° C., or any of about 21° C. to about 50° C., about 25° C. to about 75° C., about 50° C. to about 100° C., about 75° C. to about 125° C., about 90° C. to about 130° C., about 21° C. to about 100° C., or about 100° C. to about 130° C.

In one embodiment, the environmental stressor is low temperature. In one embodiment, the atmospheric temperature is about −200° C. to about 21° C. In some embodiments, the atmospheric temperature is any of at least about −200° C., −175° C., −150° C., −125° C., −100° C., −75° C., −50° C., −25° C., 0° C., or 15° C., of any of about −200° C. to about −175° C., about −175° C. to about −150° C., about −125° C. to about −100° C., about −100° C. to about −75° C., about −75° C. to about −50° C., about −50° C. to about −25° C., about −25° C. to about 0° C., about 0° C. to about 21° C., or about −200° C. to about −100° C., about −100 to about 0° C., or about −50° C. to about 21° C.

In one embodiment, the environmental stressor is ultraviolet light. In one embodiment, the ultraviolet light duration is at least about half a second and no longer than about two minutes. In some embodiments, the ultraviolet light duration is any of at least about 0.5, 1, 5, 10, 50, or 100 seconds, or any of about 0.5 to about 1, about 1 to about 5, about 2 to about 10, about 5 to about 25, about 15 to about 50, about 25 to about 75, about 80 to about 120, about 0.5 to about 50, about 25 to about 120, or about 60 to about 120 seconds.

In one embodiment, the environmental stressor is osmotic pressure. In one embodiment, the osmotic stressor added to the growth medium is a salt such as sodium chloride at a concentration of about 5 mM to about 10 M. In one embodiment the osmotic stressor added to the growth medium is a sugar such as glucose at a concentration of about 5 mM to about 10 M. In some embodiments, the osmotic stressor is included in the growth medium at a concentration of any of at least about 5 mM, 10 mM, 50 mM, 100 mM, 250 mM, 500 mM, 750 mM, 1 M, 2.5 M, 5 M, 7.5 M, or 9.5 M, or any of about 5 mM to about 25 mM, about 10 mM to about 50 mM, about 25 mM to about 75 mM, about 50 mM to about 100 mM, about 75 mM to about 150 mM, about 100 mM to about 500 mM, about 250 mM to about 750 mM, about 500 mM to about 1 M, about 750 mM to about 1.5 M, about 1 M to about 2.5 M, about 2 M to about 5 M, about 2.5 M to about 7.5 M, about 5 M to about 1 M, about 5 mM to about 100 mM, about 100 mM to about 1 M, or about 1 M to about 10 M.

In one embodiment, the environmental stressor is an inorganic chemical. In one embodiment, the inorganic chemical added to the growth medium is at a concentration of at least about 1 pg/ml to about 1 g/ml. In some embodiments, the inorganic chemical is included in the growth medium at a concentration of any of at least about 1 pg/ml, 10 pg/ml, 50 pg/ml, 100 pg/ml, 500 pg/ml, 750 pg/ml, 1 ng/ml, 10 ng/ml, 50 ng/ml 100 ng/ml 500 ng/ml, 750 ng/ml, 1 µg/ml, 10 µg/ml, 50 µg/ml, 500 µg/ml, 750 µg/ml, 1 mg/ml, 10 mg/ml, 50 mg/ml, 100 mg/ml, 500 mg/ml, 750 mg/ml or 950 mg/ml, or any of about 1 pg/ml to about 500 pg/ml, about 250 pg/ml to about 750 pg/ml, about 500 pg/ml to about 1 ng/ml, about 750 pg/ml to about 250 ng/ml, about 1 ng/ml to about 500 ng/ml, about 250 ng/ml to about 750 ng/ml, about 500 ng/ml to about 1 µg/ml, about 250 µg/ml to about 750 µg/ml, or about 500 µg/ml to about 1 mg/ml, about 750 µg/ml to about 250 mg/ml, about 250 mg/ml to about 750 mg/ml about 500 mg/ml to about 1 g/ml, about 1 pg/ml to about 1 ng/ml, about 1 ng/ml to about 1 µg/ml, about 1 µg/ml to about 1 mg/ml, or about 1 mg/ml to about 1 g/ml. In some embodiments, the inorganic chemical is aluminum oxide, cerium oxide, zinc oxide, silicon dioxide, titanium oxide, chlorine dioxide, iron chloride, copper sulfate, silver nanoparticles, or cobalt oxide.

In one embodiment, the environmental stressor is ionizing radiation. In one embodiment, self-contained irradiation units from J. L. Shepherd with Cobalt 60 or Cesium 137 is used to irradiate about 0.1 ml to about 1 liter inoculated samples with radiation as low as about 1 Gy/min to as high as about 250 Gy/min. In some embodiments, the radiation level is any of at least about 1 Gy/min, 5 Gy/min, 10 Gy/min, 25 Gy/min, 50 Gy/min, 125 Gy/min, 150 Gy/min, 175 Gy/min, 200 Gy/min, 225 Gy/min, or 245 Gy/min, or about 1 Gy/min, to about 5 Gy/min, about 2.5 Gy/min to about 7.5 Gy/min, about 5 Gy/min to about 10 Gy/min, about 7.5 Gy/min to about 25 Gy/min, about 10 Gy/min to about 50 Gy/min, about 25 Gy/min to about 75 Gy/min, about 50 Gy/min to about 100 Gy/min, about 75 Gy/min to about 150 Gy/min, about 100 Gy/min to about 150 Gy/min, about 125 Gy/min to about 175 Gy/min, about 150 Gy/min to about 200 Gy/min, about 175 Gy/min to about 250 Gy/min, about 1 Gy/min to about 50 Gy/min, about 50 Gy/min to about 150 Gy/min, about 100 Gy/min to about 200 Gy/min, or about 150 Gy/min to about 250 Gy/min.

In one embodiment, the environmental stressor is the composition of atmospheric gas. In one embodiment, oxygen ($O_2$) is added to the atmosphere, e.g., to an anaerobic atmosphere, at a concentration of at least about 0.2% v/v to about 100% v/v. In some embodiments, the oxygen is added to the atmosphere at a concentration of any of at least about 1% v/v, 5% v/v, 10% v/v, 20% v/v, 30% v/v, 40% v/v, 50% v/v, 60% v/v, 70% v/v, 80% v/v, or 85% v/v, or 90% v/v, or 95% v/v, or any of about 1% v/v to about 5% v/v, about 2.5% v/v to about 10% v/v, about 5% v/v to about 20% v/v, about 10% v/v to about 25% v/v, about 20% v/v to about 50% v/v, about 40% v/v to about 60% v/v, about 50% v/v to about 75% v/v, about 70% v/v to about 85% v/v, about 75% v/v to about 100% v/v, about 1% v/v to about 40% v/v, about 25% v/v to about 60% v/v, about 10% v/v to about 70% v/v, or about 50% v/v to about 100% v/v. In another embodiment, the atmospheric oxygen is limited to a concentration of 0% or substantially 0% v/v.

In one embodiment, the environmental stressor is a vitamin or co-factor, or lack thereof. In some embodiments, the vitamin or co-factor is not included in the growth medium (0%) or is limited to a very low level (substantially 0% w/w). In one embodiment, vitamin or co-factor is biotin, for example, at a concentration of 0% or limited to substantially 0% w/w.

In one embodiment, the environmental stressor is an acid. In one embodiment, the amount of added acid is at a concentration of about 0.1 mM to about 10 M. In some embodiments, the acid is included in the growth medium at a concentration of any of at least about 0.1 mM, 0.5 mM, 1 mM, 5 mM, 10 mM, 50 mM, 100 mM, 250 mM, 500 mM, 750 mM, 1 M, 2.5 M, 5 M, 7.5 M, or 9.5 M, or any of about 0.1 mM to about 0.5 mM, about 0.25 mM to about 0.75 mM, about 0.5 mM to about 1 mM, about 0.75 mM to about 1.25 mM, about 1 mM to about 5 mM, about 2.5 mM to about 10 mM, about 1.5 mM to about 25 mM, about 10 mM to about 50 mM, about 25 mM to about 75 mM, about 50 mM to about 100 mM, about 75 mM to about 150 mM, about 100 mM to about 500 mM, about 250 mM to about 750 mM, about 500 mM to about 1 M, about 750 mM to about 1.5 M, about 1 M to about 2.5 M, about 2 M to about 5 M, about 2.5 M to about 7.5 M, about 5 M to about 1 M, about 0.1 mM to about 1 mM, about 1 mM to about 10 mM, about 5 mM to about 100 mM, about 100 mM to about 1 M, or about 1 M to about 10 M. In some embodiments, the acid is ethylenediaminetetraacetic acid (EDTA), lactic acid, hydrochloric acid, sulfuric acid, butyric acid, sorbic acid, sulfurous acid, boric acid, citric acid, nitrous acid, nitric acid, carbonic acid, benzoic acid, ascorbic acid, iso-ascorbic acid, acetic acid, salicylic acid, aspirin, sulfadiazine, ibuprofen, phosphoric acid, erythorbic acid, propionic acid, tartaric acid, perchloric acid, hydrobromic acid, hydroiotic acid, hydrocyanic, hydrofluoric acid, phosphorous acid, hydroselenic acid, hydrosulfuric acid, or oxalic acid.

In one embodiment, the environmental stressor is a base used to increase the pH. In one embodiment, the amount of added base is at a concentration of about 0.1 mM to about 10 M. In some embodiments, the base is included in the growth medium at a concentration of any of at least about 0.1 mM, 0.5 mM, 1 mM, 5 mM, 10 mM, 50 mM, 100 mM, 250 mM, 500 mM, 750 mM, 1 M, 2.5 M, 5 M, 7.5 M, or 9.5 M, or any of about 0.1 mM to about 0.5 mM, about 0.25 mM to about 0.75 mM, about 0.5 mM to about 1 mM, about 0.75 mM to about 1.25 mM, about 1 mM to about 5 mM, about 2.5 mM to about 10 mM, about 1.5 mM to about 25 mM, about 10 mM to about 50 mM, about 25 mM to about 75 mM, about 50 mM to about 100 mM, about 75 mM to about 150 mM, about 100 mM to about 500 mM, about 250 mM to about 750 mM, about 500 mM to about 1 M, about 750 mM to about 1.5 M, about 1 M to about 2.5 M, about 2 M to about 5 M, about 2.5 M to about 7.5 M, about 5 M to about 1 M, about 0.1 mM to about 1 mM, about 1 mM to about 10 mM, about 5 mM to about 100 mM, about 100 mM to about 1 M, or about 1 M to about 10 M. In some embodiments the base is lithium hydroxide, sodium hydroxide, potassium hydroxide, rubidium hydroxide, cesium hydroxide, magnesium hydroxide, calcium hydroxide, strontium hydroxide, barium hydroxide, butyl lithium, lithium diisopropylamide, lithium diethylamide, sodium amide, sodium hydride, lithium bis(trimethylsilyl)amide, a mixture of silicon dioxide and aluminum hydroxide, a mixture of magnesium oxide and silicon dioxide, a mixture of calcium oxide and silicon dioxide, activated charcoal, calcium carbonate, sodium bicarbonate, sodium carbonate (soda ash), bone char, ammonium hydroxide, ammonia, aniline, methylamine, dimethylamine, triethylamine, ethylamine, dietheylamine, triethylamine, dibutylamine, tributylamine, n-butylamine, hypochorite, cyanide, phosphate, silicate, hydroxide, alpyridine, codeine, amphetamine, or epinephrine.

In one embodiment, the environmental stressor is the carbohydrate source. In one embodiment, the amount of carbohydrate source that the parent can metabolize for growth in the growth medium is limited to a concentration of 0% or substantially 0% w/w.

In one embodiment, the environmental stressor is the nitrogen source. In some embodiments, the nitrogen source is not included in the growth medium (0%) or is limited to a very low level (substantially 0% w/w). In one embodiment, the nitrogen source is one or more amino acid(s) or protein(s) in the growth medium, for example, at a concentration of 0% or limited to substantially 0% w/w.

In one embodiment, the environmental stressor is a biological toxin. In one embodiment, the toxin is included in the growth medium at a concentration of about 100 pg/ml to about 1 g/ml. In some embodiments, the biological toxin is included in the growth medium at a concentration of any of at least about 100 pg/ml, 250 pg/ml, 500 pg/ml, 750 pg/ml, 1 ng/ml, 10 ng/ml, 50 ng/ml 100 ng/ml 500 ng/ml, 750 ng/ml, 1 µg/ml, 10 µg/ml, 50 µg/ml, 500 µg/ml, 750 µg/ml, 1 mg/ml, 10 mg/ml, 50 mg/ml, 100 mg/ml, 500 mg/ml, 750 mg/ml, or 950 mg/ml, or any of about 100 pg/ml to about 500 pg/ml, about 250 pg/ml to about 750 pg/ml, about 500 pg/ml to about 1 ng/ml, about 750 pg/ml to about 250 ng/ml, about 1 ng/ml to about 500 ng/ml, about 250 ng/ml to about 750 ng/ml, about 500 ng/ml to about 1 µg/ml, about 250 µg/ml to about 750 µg/ml, or about 500 µg/ml to about 1 mg/ml, about 750 µg/ml to about 250 mg/ml, about 250 mg/ml to about 750 mg/ml about 500 mg/ml to about 1 g/ml, about 100 pg/ml to about 1 ng/ml, about 1 ng/ml to about 1 µg/ml, about 1 µg/ml to about 1 mg/ml, or about 1 mg/ml to about 1 g/ml. In one embodiments, the toxin is Toxin A, B, or CDT from *C. difficile*, for example, at a concentration of at least about 100 ng/ml. In some embodiments the toxin is an exotoxin, enterotoxin, or endotoxin produced by a bacterial species.

In one embodiment, the environmental stressor is a peptide, for example, a microbial peptide. In one embodiment, the peptide is included in the growth medium at a concentration of about 10 mg/kg to about 1 g/kg. In some embodiments, the peptide is included in the growth medium at a concentration of any of at least about 1 mg/kg, 10 mg/kg, 50 mg/kg, 100 mg/kg, 250 mg/kg, 500 mg/kg, 600 mg/kg, 700 mg/kg, 800 mg/kg, 900 mg/kg, or 950 mg/kg, or any of about 1 mg/kg to about 10 mg/kg, about 5 mg/kg to about 25 mg/kg, about 10 mg/kg to about 50 mg/kg, about 25 mg/kg to about 75 mg/kg, about 50 mg/kg to about 100 mg/kg, about 75 mg/kg to about 200 mg/kg, about 100 mg/kg to about 250 mg/kg, about 150 mg/kg to about 300 mg/kg, about 250 mg/kg to about 500 mg/kg, about 350 mg/kg to about 600 mg/kg, about 500 mg/kg to about 750 mg/kg, about 600 mg/kg to about 900 mg/kg, about 750 mg/kg to about 1000 mg/kg, about 1 mg/kg to about 250 mg/kg, about 1 mg/kg to about 500 mg/kg, about 250 mg/kg to about 750 mg/kg, or about 500 mg/kg to about 1000 mg/kg. In some embodiments, the peptide is a bacteriocin, anti-toxin, antigen, or quorum-sensing peptide.

In one embodiment, the environmental stressor is a preservative substance, e.g., a food preservative substance. In one embodiment, the preservative substance is included in the growth medium at a concentration of about 0.5 mM to about 1 M. In some embodiments, the preservative substance is included in the growth medium at a concentration of any of at least about 0.5 mM, 1 mM, 5 mM, 10 mM, 25 mM, 50 mM, 100 mM, 250 mM, 500 mM, 750 mM, or 1 M, or any of about 0.5 mM to about 0.25 mM, about 1 mM to about 5 mM, about 2.5 mM to about 7.5 mM, about 5 mM to about 10 mM, about 7.5 mM to about 15 mM, about 10 mM to about 50 mM, about 25 mM to about 75 mM, about 50 mM to about 100 mM, about 75 mM to about 150 M, about 100 mM to about 250 mM, about 200 mM to about 500 mM, about 250 mM to about 75 mM, about 500 mM to about 100 mM, about 500 mM to about 1 M, or about 100 mM to about 1 M. In some embodiments, the preservative substance is potassium nitrate, potassium nitrite, sodium ascorbate, sodium erythorbate, calcium ascorbate, sodium iso-ascorbate, sodium nitrate, sodium nitrite, wood smoke, calcium sorbate, ethyl lauroyl arginate, 4-hexylresorcinol, methyl-p-hydroxy benzoate, methyl paraben, potassium benzoate, potassium bisulphite, potassium lactate, potassium metabisulphite, potassium sorbate, propyl-p-hydroxy benzoate, propyl paraben, sodium acetate, sodium benzoate, sodium bisulphite, sodium diacetate, sodium lactate, sodium metabisulphite, sodium sorbate, sodium sulphite, sodium dithionite, calcium propionate, calcium sorbate, dimethyl dicarbonate, natamycin, potassium sorbate, sodium diacetate, sodium proprionate, sodium sorbate, ascorbyl palmitate, ascorbyl stearate, butylated hydroxyanisole, butylated hydroxytoluene, L-cysteine, L-cysteine hydrochloride, gum guaiacum, lecithin, lecithin citrate, monoglyceride citrate, monoisopropyl citrate, propyl gallate, sodium metabisulphite, tertiary butyl hydroquinone, or a tocopherol.

In one embodiment, the environmental stressor is an herbicide. In one embodiment, the herbicide is included in the growth medium at a concentration of about 1 pg/kg to about 1 g/kg. In some embodiments, the herbicide is included in the growth medium at a concentration of any of at least about 1 pg/kg, 10 pg/ml, 50 pg/kg, 100 pg/kg, 500 pg/kg, 750 pg/kg, 1 ng/kg, 10 ng/kg, 50 ng/kg, 100 ng/kg 500 ng/kg, 750 ng/kg, 1 µg/kg, 10 µg/kg, 50 µg/kg, 500 µg/kg, 750 µg/kg, 1 mg/kg, 10 mg/kg, 50 mg/kg, 100 mg/kg, 500 mg/kg, 750 mg/kg, or 950 mg/kg, or any of about 1 pg/kg to about 500 pg/kg, about 250 pg/kg to about 750 pg/kg, about 500 pg/kg to about 1 ng/kg, about 750 pg/kg to about 250 ng/kg, about 1 ng/kg to about 500 ng/kg, about 250 ng/kg to about 750 ng/kg, about 500 ng/kg to about 1 µg/kg, about 250 µg/kg to about 750 µg/kg, or about 500 µg/kg to about 1 mg/kg, about 750 µg/kg to about 250 mg/kg, about 250 mg/kg to about 750 mg/kg, about 500 mg/kg to about 1 g/kg, about 1 pg/kg to about 1 ng/kg, about 1 ng/kg to about 1 µg/kg, about 1 µg/kg to about 1 mg/kg, or about 1 mg/kg to about 1 g/kg. In some embodiments, the herbicide is atrazine, nicosulfuron, carfentrazone, naptalam, 2,4-dichlorophenoxyacetic acid (2-4 D), quizalofop, benefin, bentazon, prometryn, mesotrione, flumioxzin, clomazone, ethalfluralin, dimethyl tetrachloroterephthalate (DCPA), napropamide, diquat, s-metolachlor, s-ethyl dipropylthiocarbamate (EPTC), ametryn, dimethenamide, fluazifop, oxylfluorfen, paraquat, diuron, pronamide, alachlor, tembotrione, linuron, rimsulfuron, sethoxydim, bensulide, pendimethalin, pyrazon, cycloate, maleic hydrazide, glyphosate, halosulfuron, plelargonic acid, clethodim, metribuzin, rimsulfuron, terbacil, ethalfluralin, phenmedipham, clopyralid, butylate, 4-(2-methyl-4-chlorophenoxy) butyric acid (MCPB), pebulate, or trifluralin.

In one embodiment, the environmental stressor is a fungicide or bacteriocide. In one embodiment, the fungicide or bacteriocide is included in the growth medium at a concentration of about 1 pg/kg to about 1 g/kg. In some embodiments, the fungicide or bacteriocide is included in the growth medium at a concentration of any of at least about 1 pg/kg, 10 pg/ml, 50 pg/kg, 100 pg/kg, 500 pg/kg, 750 pg/kg, 1 ng/kg, 10 ng/kg, 50 ng/kg, 100 ng/kg 500 ng/kg, 750 ng/kg, 1 µg/kg, 10 µg/kg, 50 µg/kg, 500 µg/kg, 750 µg/kg, 1 mg/kg, 10 mg/kg, 50 mg/kg, 100 mg/kg, 500 mg/kg, 750 mg/kg, or 950 mg/kg, or any of about 1 pg/kg to about 500 pg/kg, about 250 pg/kg to about 750 pg/kg, about 500 pg/kg to about 1 ng/kg, about 750 pg/kg to about 250 ng/kg, about 1 ng/kg to about 500 ng/kg, about 250 ng/kg to about 750 ng/kg, about 500 ng/kg to about 1 µg/kg, about 250 µg/kg to about 750 µg/kg, or about 500 µg/kg to about 1 mg/kg, about 750 µg/kg to about 250 mg/kg, about 250 mg/kg to about 750 mg/kg, about 500 mg/kg to about 1 g/kg, about 1 pg/kg to about 1 ng/kg, about 1 ng/kg to about 1 µg/kg, about 1 µg/kg to about 1 mg/kg, or about 1 mg/kg to about 1 g/kg. In some embodiments, the fungicide or bacteriocide is acibenzolar-S-methyl, streptomycin sulfate, bacteriophage, fosetyl A1, mefenoxam, potassium bicarbonate, copper oxychloride, copper hydroxide, copper sulfate, pentachloronitrobenzene (PCNB), dichloran, propiconazole, pyraclostrobin, copper octonate, copper hydroxide, chlorothalonil, cymoxanil, fenhexamid, boscalid, trifloxystrobin, penthiopyrad, dimethomorph, trifloxystrobin, paraffinic oil, cupric hydroxide, fluopyram, mancozeb, fludioxonil thiabendazole, mandipropamid, sulfur, potassium bicarbonate, monopotassium phosphate, fluazinam, polyoxin D, hydrogen dioxide, potassium phosphate, fluopicolide, propamocarb, triflumizole, azoxystrobin, quinoxyfen, myclobutanil, cyazofamid, femadione, mandipropamid, mefenoxam, iprodione, pyrimethanil, petroleum oil, or metrofenone.

In one embodiment, the environmental stressor is a pesticide. In one embodiment, the pesticide is included in the growth medium at a concentration of about 1 pg/kg to about 1 g/kg. In some embodiments, the pesticide is included in the growth medium at a concentration of any of at least about 1 pg/kg, 10 pg/ml, 50 pg/kg, 100 pg/kg, 500 pg/kg, 750 pg/kg, 1 ng/kg, 10 ng/kg, 50 ng/kg, 100 ng/kg 500 ng/kg, 750 ng/kg, 1 µg/kg, 10 µg/kg, 50 µg/kg, 500 µg/kg, 750 µg/kg, 1 mg/kg, 10 mg/kg, 50 mg/kg, 100 mg/kg, 500 mg/kg, 750 mg/kg, or 950 mg/kg, or any of about 1 pg/kg to about 500 pg/kg, about 250 pg/kg to about 750 pg/kg, about 500 pg/kg to about 1 ng/kg, about 750 pg/kg to about 250 ng/kg, about 1 ng/kg to about 500 ng/kg, about 250 ng/kg to about 750 ng/kg, about 500 ng/kg to about 1 µg/kg, about 250 µg/kg to about 750 µg/kg, or about 500 µg/kg to about 1 mg/kg, about 750 µg/kg to about 250 mg/kg, about 250 mg/kg to about 750 mg/kg, about 500 mg/kg to about 1 g/kg, about 1 pg/kg to about 1 ng/kg, about 1 ng/kg to about 1 µg/kg, about 1 µg/kg to about 1 mg/kg, or about 1 mg/kg to about 1 g/kg. In some embodiments the pesticide is abamectin, acephate, bifenazate, thiamethoxam, imidacloprid, fenpyroximate, imidacloprid, azadirachtin, permethrin, malathion, esfenvalerate, acetamiprid, indoxacarb, azadirachtin, beta-cyfluthrin, clothianidin, flonicamid, flubendiamide, bifenthrin, spinosad, carbaryl, chlorpyrifos, sulfoxaflor, tebufenozide, chlorantraniliprole, terbufos, thiamethoxam, mineral oil, fenpropathrin, metaldehyde, gamma-cyhalothrin, deltamethrin, diazinon, dimethoate, diflubenzuron, pyriproxyfen, cyantraniliprole, bifenazate, tefluthrin, pymetrozine, chlorpyrifos, zeta-cypermethrin, phosmet, methoxyfenozide, acequinocyl, lambda-cyhalothrin, imidacloprid, malathion, soybean oil, sulfur, spirotetramat, oxydemeton-methyl, cyflumetofen, spiromesifen, emamectin benzoate, cryolite, chlorfenapyr, pyrethrins, fipronil, novaluron, dinotefuran, cottonseed oil, acequinocyl, iron phosphate, buprofezin, neem oil, cyromazine, oxamyl, or etoxazole.

In one embodiment, the environmental stressor is a filtrate of another microbe's spent fermentation broth. For example, in one embodiment, filtered spent broth from a *Clostridium difficile* fermentation is used as a stressor. In one embodiment, the filtered spent broth is added to the growth medium at a concentration of about 1% v/v to about 90% v/v. In some embodiments, the spend broth is included in the growth medium at a concentration of any of at least about 1% v/v, 5% v/v, 10% v/v, 20% v/v, 30% v/v, 40% v/v, 50% v/v, 60% v/v, 70% v/v, 80% v/v, or 85% v/v, or any of about 1% v/v to about 5% v/v, about 2.5% v/v to about 10% v/v, about 5% v/v to about 20% v/v, about 10% v/v to about 25% v/v, about 20% v/v to about 50% v/v, about 40% v/v to about 60% v/v, about 50% v/v to about 75% v/v, about 70% v/v to about 85% v/v, about 75% v/v to about 90% v/v, about 1% v/v to about 40% v/v, about 25% v/v to about 60% v/v, about 10% v/v to about 70% v/v, or about 50% v/v to about 90% v/v.

A parental microbial strain may be bacterial or fungal. In some embodiments, the microbial strain is a species of *Lactobacillus, Pediococcus, Streptococcus, Lactococcus,*

*Leuconostoc, Oenococcus, Weissella, Bifidobacterium, Gardnerella, Clostridium, Deionococcus, Faecalibacterium, Anaerobacter, Coprobacillus, Oxobacter, Sporobacter, Eubacterium, Heliobacterium, Oscillospira, Peptococcus, Dehalobacter, Butyrivibrio, Coprococcus, Lachnospira, Ruminococcus, Peptostreptococcus, Moorella, Listeria, Mycoplasma, Bacillus, Paenibacillus, Staphylococcus, Enterococcus, Enterobacter, Escherichia, Salmonella, Klebsiella, Pseudomonas, Vibrio, Helicobacter, Haemophilus, Halomonas, Bacteroides, Prevotella, Bartonella, Porphyromonas, Actinomyces, Streptomyces, Corynebacterium, Propionibacterium, Mycobacterium, Caulobacter, Bradyrhizobium, Agrobacterium, Rhodobacter, Rhodopseudomonas, Magnetospirillum, Magnetobacterium, Acetobacter, Zymomonas, Rikettsia, Eleftheria, Saccharomyces, Schizosacchoromyces, Schefferomyces, Zygosaccharomyces, Yarrowia, Pichia, Dekkera, Kluyveromyces, Candida, Metschnikowia,* or *Torulaspora*. In one embodiment, the bacterial strain is a *Lactobacillus* species, for example, *L. plantarum, L. delbrueckii, L. acidophilus, L. brevis, L. casei, L. sanfranciscensis, L. rhamnosus, L. helveticus, L. curvatus, L. sakei, L. buchneri, L. fermentum,* or *L. reuteri*.

In some embodiments, the parental strains are not classified in the same kingdom. In one embodiment, the parental strains are not classified in the same phylum.

In some embodiments, both the intended parental host and donor strains have different environmental stressors applied in tandem.

In some embodiments, the pre-stressor applied is of a different variety (e.g., different selective agent or environmental condition) from the selective environment of the gene transfer.

In some embodiments, the parent intended to be the donor strain can become the host.

Some embodiments result in microbial hybrids that retain some genes from both parents.

Some embodiments result in microbial hybrids that are polyploidal, i.e. retaining the entire genomes or substantially the entire genomes from both parents.

In some embodiments, the microbial hybrid genotypes as the species of one of the two microbial parent strains from which it is derived. For example, even though the microbial hybrid contains DNA from both microbial parents, it may retain the 16S rRNA from only one parent, thereby genotyping as the species of that parent.

Resulting microbial hybrids have undergone horizontal gene transfer without the use of a vector.

Microbial hybrids are considered to be chimeric.

The resulting microbial hybrids (from a single colony) may display multiple phenotypes depending on the environment in which they are grown.

Chimeric Microbial Hybrids

Chimeric microbial hybrids are the resulting strains from the methods disclosed herein, and which have hybrid phenotypes and genotypes. They are the result of in vitro lateral gene transfer without the use of vectors. Chimeric microbes retain and express DNA from both the parental host and parental donor.

In one embodiment, chimeric microbial hybrids can be confirmed by comparing the phenotypes or genotypes of the parental hosts with the parental donor. In some embodiments, host strains will share any of about 0.01%, 0.1%, 1%, 10%, 20%, 30%, 40%, 50%, 60%, 70%, 80%, 90%, 95%, 98%, 99%, or 100%, or any of at least about 0.01%, 0.1%, 1%, 10%, 20%, 30%, 40%, 50%, 60%, 70%, 80%, 95%, 98%, or 99%, of chromosomal genes with the parental donor strain.

In some embodiments, chimeric microbial hybrids are confirmed by phenotypic tests such as checking carbon sources for metabolism, growth on dual selection plates whereupon both parental strains cannot grow, or whole genome sequencing which shows exactly which genes were gained and/or lost during gene transfer.

Methods of Use for Chimeric Microbial Hybrids

Chimeric microbial hybrids have many commercial and industrial applications. Adding or subtracting traits to create new commodities or improve the profitability of current commercial microbes include a wide range of operative uses and production of commodities in such industries including, but not limited to, alcohol production, fermented food products, herbicide production, fungicide production, bacteriocide production, pesticide production, food additives and preservatives, biofuel and biochemical production, probiotics, live biotherapeutics, medicinal foods, and pharmaceuticals.

In some embodiments, the strain improvement methods disclosed herein may be used to make chimeric strains which are better suited (e.g., have improved fitness in comparison to wild type strains) to make new commodities in the fermented food industry. In one embodiment, prized industrial traits such as high temperature resistance in a microorganism such as *Streptococcus thermophilus* could be transferred to other organisms whose fermentations result in differently flavored dairy products such as cheese or yogurt.

In some embodiments, the strain improvement methods disclosed herein may be used to make chimeric strains which make industrial commodities that wild type strains of the same 16S rRNA genotyping cannot make. In some embodiments, commodities can include, but are not limited to, production of biomass or cellular material; production of extracellular metabolites such as bacteriocins, solvents or other chemical compounds; production of intracellular components such as enzymes, proteases or other proteins; or transformation of the fermentation substrate such as in yogurt or cheese.

In some embodiments, the strain improvement methods disclosed herein may be used to make chimeric strains which are better suited than wild type strains to be used as general health probiotics. Traits such as ability to sporulate, faster growth, high temperature resistance, and acid tolerance could improve the efficacy of current probiotics.

In some embodiments, the strain improvement methods disclosed herein may be used to make chimeric strains which are better suited than wild type strains as live biotherapeutics to treat diseases or conditions including, but not limited to urogenital infections; intestinal inflammation including inflammatory bowel syndrome, irritable bowel syndrome, colitis, and Crohn's disease; enterotoxin mediated infection such as cholera; antibiotic-associated diarrhea (AAD) including *Clostridium difficile* infections; acute diarrhea; food poisoning; atopic dermatitis including eczema; acne; bacterial vaginosis; yeast infections; toxic shock syndrome; necrotizing enterocolitis (NEC); tooth decay; vitamin deficiencies; hypertension; high cholesterol; ulcers; obesity; childhood respiratory infections; nasal pathogens; allergies; autoimmune diseases including rheumatoid arthritis, type I diabetes, multiple sclerosis, vasculitis, alopecia areata, lupus, polymyalgia rheumatica, ankylosing spondylitis, temporal arteritis, Sjögren's syndrome, celiac disease, Graves' disease, and Hashimoto's thryoiditis; lactose intolerance; type II diabetes; drug resistant bacterial infections such as methicillin resistant *Staphylococcus aureus* (MRSA); gout; an infectious disease; heart disease and cancers.

In some embodiments, chimeric strains may be used to prevent and treat *Clostridium difficile* Infection (CDI). New traits such as amino acid prototrophy and starch metabolism will support growth in low-nutritive environments such as those present during an intestinal infection. Other traits, such as increased adhesion to colonic epithelial cells, anti-toxin A production, anti-toxin B production or bacteriocin production can also be added to wild-type strains to induce therapeutic qualities for CDI treatment.

The following examples are intended to illustrate, but not limit, the invention.

EXAMPLES

Example 1

*Lactobacillus plantarum* Amino Acid Auxotrophy Removal with Ethanol Pre-Stressor The desired parental host in this experiment was *Lactobacillus plantarum*. The phenotype to be acquired was provided by the parental donor, *Clostridium beijerinckii*. The desired trait for genetic transfer was amino acid prototrophy, or survival on a minimal medium containing no proteins or amino acids; the clostridial parent can grow on minimal medium at 35-37° C. anaerobically. The *Lactobacillus* parent cannot grow on a medium without proteins or added amino acids.

MICs for stressors were determined. *C. beijerinckii's* optimal temperature for growth is 32° C. with an MIC of 39° C. *L. plantarum* has an optimal temperature for growth at 37° C. with an MIC of 44° C. Selected gene transfer medium was a minimal medium that did not contain amino acids or proteins. The *Clostridium* parent is an obligate anaerobe whereas the *Lactobacillus* parent is a facultative anaerobe. The chosen atmospheric conditions for this gene transfer were aerobic with an anaerobic start. Post-gene transfer, plates were moved to an aerobic incubator set to 42° C.

Pre-stressor conditions included several solvents, including ethanol, at several concentrations, up to 0.2 M. A control without the use of pre-stressors was also performed.

The medium for all cultures was a modified Reinforced Clostridial Medium (RCM) with 2% w/w glucose. Prior to applying the pre-stressors, cultures were grown up in the same modified RCM to an $OD_{600}$ of 1.0 in an anaerobic chamber at 37° C.

Equivalent starting CFUs for the parental host, *L. plantarum*, were $2.5\times10^{8}$ CFU/ml, for a total volume of 5 ml containing $1.25\times10^{9}$ cells. Meanwhile, the desired donor, *C. beijerinckii*, had equivalent CFUs of $1\times10^{8}$ CFU/ml, for a total volume of 5 ml containing $5\times10^{8}$ cells.

Following the 30-minute incubation with or without pre-stressors, both parent cultures were mixed together for each condition and filtered on to a sterile, 0.2 μm filter. Filters were then washed via syringe with 10 ml of sterile PBS. Each filter was placed upside down on to a deoxygenated, minimal medium plate. Plates were taken out of the anaerobic chamber and put into an aerobic incubator set at 42° C. Plates were incubated for 48 hours.

After 48 hours, filters from each condition were removed from agar plates and placed into 1 ml of PBS inside a 1.5 ml microcentrifuge tube. Microcentrifuge tubes containing the filters were vortexed and then spun down at 8000 RFC for 10 minutes. 800 ml of supernatant were removed, and the cell pellet was resuspended in the remaining 200 μl of supernatant. The entire suspension for each condition was then plated on to a single, fresh, aerobic minimal plate taken into the anaerobic chamber immediately prior to plating. Once plates were dry, they were taken out of the chamber and placed into an aerobic incubator set to 42° C.

Plates were checked daily for colonies. Single colonies were then re-streaked from a single colony at 3-5 days post plating on two different plates, one minimal medium plate, and one rich medium. After two days, single colonies were restreaked again from the rich medium plates to minimal plates. Only colonies that restreaked, and grew once again to single colonies on the final set of minimal medium plates, were then analyzed.

Results

The frequency of gene transfer resulting in a prototrophic hybrid was $1\times10^{-8}$ for the 200 mM ethanol pre-stressor condition. No colonies resulted from the condition without an applied pre-stressor. Analysis of the resulting chimeric microbial hybrid, C-1, was done in parallel with the nine chimeras from Example 2. Example 2, below, provides more detailed results.

Example 2

*L. plantarum* Amino Acid Auxotrophy Removal with UV Pre-Stressor

The desired parental host was *Lactobacillus plantarum*. The desired phenotype to be transferred was provided by the parental donor, *Clostridium beijerinckii*. The desired trait for genetic transfer was amino acid prototrophy, or survival on a minimal medium plate containing no proteins or amino acids.

*C. beijerinckii* can grow on minimal medium at 35° C. anaerobically. *L. plantarum* cannot grow on a medium without proteins or added amino acids. *C. beijerinckii*'s optimal temperature for growth is 32° C. with an MIC of 39° C. The *Lactobacillus* parent strain has an optimal temperature for growth at 37° C. with an MIC of 44° C. Selected gene transfer medium was a minimal medium that contained no proteins or amino acids.

Pre-stressors included two different conditions with short bursts of ultraviolet (UV) light. One condition applied UV light inside in an aerobic biosafety cabinet in open petri dishes, for 3×2 second intervals with 10 minutes of rest between cycles for both parents. A second condition applied the same UV stressor for only the *Lactobacillus* parent, with no stressor for the *Clostridium* parent and continued anaerobic incubation at 35° C. All strains were pre-stressed in separate cultures along with a condition where both parents continued incubation inside an anaerobic chamber at 35° C. for 30 minutes with no pre-stressor applied.

The medium for all cultures was a modified RCM with 2% w/w glucose. Prior to applying the pre-stressors, cultures were grown up in the same modified RCM to an $OD_{600}$ of 1.0 in an anaerobic chamber at 35° C. Equivalent starting CFUs for the host *Lactobacillus plantarum* strain, were $2.5\times10^{8}$ CFU/ml, for a total volume of 5 ml containing $1.25\times10^{9}$ cells. Meanwhile, the desired donor *Clostridium beijerinckii* strain had equivalent CFUs of $1\times10^{8}$ CFU/ml, for a total volume of 5 ml containing $5\times10^{8}$ cells.

Following the 30-minute incubation with or without pre-stressors, both parent cultures were mixed together for each condition and filtered on to a 0.2 μm filter. Filters were then washed via syringe with 10 ml of sterile PBS. Filters were placed upside down on to a deoxygenated, minimal medium plate. Plates were put inside a mostly air-tight box without an oxygen removing catalyst and then taken out of the anaerobic chamber and put into an aerobic incubator set at 42° C. Plates were incubated for 48 hours. The exact oxygen percentage inside the incubation box was not measured.

After incubation, filters from each condition were placed into 1 ml of PBS inside a 1.5 ml microcentrifuge tube. Microcentrifuge tubes containing the filters were vortexed and then spun down at 8000 RFC for 10 minutes. 800 ml of supernatant were removed, and the cell pellet was resuspended in the remaining 200 µl of supernatant. The entire suspension for each condition was then plated on to a single, fresh, aerobic minimal plate taken into the anaerobic chamber immediately prior to the gene transfer. Once plates were dry, they were put into a de-oxygenated mostly air-tight box without an oxygen removing catalyst and then placed into an aerobic incubator set to 42° C.

Plates were checked daily for colonies. Single colonies were then re-streaked at 3-5 days post plating from a single colony on to two different plates, one comprised of minimal medium and one comprised of rich medium. After two days, single colonies were restreaked again from the rich medium plates to minimal plates. Only colonies that grew to single colony status on the final set of minimal medium plates were then analyzed.

Results

The frequency of gene transfer resulting in a prototrophic hybrid was $1 \times 10^{-8}$ for the Lactobacillus only UV pre-stressor. This was the same frequency observed in Example 1 for 200 mM ethanol. Successful prototrophic hybrids in the dual UV pre-stressor condition had an increased frequency of $5 \times 10^{-8}$. Finally, the condition with no pre-stressor for either parent had a frequency of $3 \times 10^{-8}$ per C. beijerinckii donor cells. Ten total strains were analyzed and found to be chimeric microbial hybrids.

First, microbial hybrids were streaked and incubated in the same dual selective environment that the original gene transfer filter was placed. FIGS. 1A-1E show growth on minimal medium (no protein or amino acids) containing bromocresol purple indicator after 72 hours at 37° C. in an anaerobic chamber. Color change from purple to yellow represents acid production and growth. The intended parental donor, Clostridium beijerinckii, is seen in FIG. 1A with robust growth. The intended parental host, Lactobacillus plantarum, is seen with no growth in FIG. 1B due to its inherent auxotrophies for several essential amino acids. A selection of three chimeric hybrids is shown in FIGS. 1C, 1D, and 1E all displaying varying degrees of growth without amino acids in the medium, confirming that they are now prototrophic for essential amino acid formation.

FIGS. 2A-2E show growth at 42° C. in an aerobic incubator after 24 hours on similar medium as FIGS. 1A-1E, but with the addition of four grams per liter yeast extract and no bromocresol purple. In these conditions, the Clostridium parent (FIG. 2A) had no growth and the Lactobacillus parent (FIG. 2B) grew. Chimeric microbial hybrids (FIGS. 2C, 2D, and 2E) grew in varying amounts showing their ability to proliferate in the presence of oxygen at higher temperatures.

FIGS. 3A-3C show the results of Biomerieux CH50 tests, which used bromocresol purple as an indicator of growth in 48 different carbohydrates. Only traits which at least one strain was positive for are included in FIGS. 3A-3C. Light grey shaded traits are specific to the Clostridium parent and black shaded traits are specific to the other parent, L. plantarum. Dark grey traits are those which both parents displayed before the gene transfer. All resulting hybrids displayed a mixture of phenotypes for carbohydrate metabolism. The number of phenotypes transferred from host to donor suggests that a large number of genes were transferred during the gene transfer. It is interesting to note that in this strain alteration method, in addition to transferring essential amino acid production genes, the transfer of additional functional genes to vary the carbon metabolism profile may also help survival in certain low nutritive environments by increasing capability to metabolize available carbohydrate sources. For instance, all of the hybrids that have the Lactobacillus morphological phenotype can now metabolize starch and sorbitol unlike their Lactobacillus parent.

Chimeric microbial hybrids were checked to see how their antibiotic resistance compared to their parents. Six antibiotics were tested on a modified Brain Heart Infusion (BHI) containing yeast extract and 5% w/w sheep's blood: amoxicillin/clavulinic acid (20 µg/10 µg), azithromycin (15 µg), carbenicillin (5 µg), ciprofloxin (5 µg), metronidazole (5 µg), and vancomycin (30 µg). 200 µl of $OD_{600}$ 0.5 cultures grown in modified BHI were spread on each plate. Plates were allowed to dry for 15 minutes. Discs containing the type and amount of antibiotic listed above were placed on the plate beginning with amoxicillin/clavulinic acid at the 12:00 position then placed clockwise in the order listed above. Plates were incubated anaerobically for 48 hours at 37° C. All of the chimeras except for C-1 retained similar susceptibilities and resistances of the Lactobacillus parent. C-1, however, given its clostridial morphology, seems to have a greater number of characteristics in common with the donor parent, suggesting that C. beijerinckii was the host instead of the donor as intended. The results are shown in FIGS. 4A-4D. The Clostridium parent (FIG. 4A) is susceptible to all six antibiotics tested. FIG. 4C clearly shows that chimera C-1 picked up one additional antibiotic resistance from the Lactobacillus parent (FIG. 4B) for metronidazole. All of the other nine chimeras retained the same results as parental Lactobacillus strain; results were all equivalent to the chimera pictured in FIG. 4D. No antibiotics were in any of the selective media before or during the gene transfer, so C-1's resistance to metronidazole was inadvertently transferred from the Lactobacillus parent.

All ten microbial hybrids were assessed for their ability to grow in rich media progressively diluted with water. A modified BHI with 5 g/L yeast extract and trace metals was serially diluted in water to assess the growth of the microbial hybrid strains in nutrient-limited media. Chimeric strains, presumably better suited in low nutrient medium as amino acid autotrophs, should perform better than their Lactobacillus parent in minimal medium. Results can be seen in FIG. 5, where all but chimera C-1 had convincing increased ability to grow in a lower total of nutrients at 37° C. It was later discovered that C-1 prefers higher temperatures (42° C.—see FIG. 2C) and most likely would have shown increased ability in both the Biomerieux assessment (FIGS. 3A-3C) and the minimal liquid media assessment (FIG. 5) if the incubation temperature had been increased.

One of the chimeras that showed particularly high protease activity toward Clostridium difficile (data not shown) was checked for growth in media designed to mimic human colonic conditions. Improved growth in medium with a high starting pH (as seen in the cecum, or first part of the large intestine), as well as overall improvement in colonic sugars, can be seen in FIG. 6 for chimera C-2. The "pH 7.6 start" medium contained 20% BHI, 1 g/L yeast extract, and 12 g/L glucose. The "+ colonic sugars" medium contained 20% BHI, 1 g/L yeast extract, 6 g/L starch, 4 g/L pectin, and 2 g/L xylan. All cultures were inoculated with $1 \times 10^6$ CFU/ml and grown for 24 hours anaerobically at 37° C. The chimeric strain, C-2, had improved growth capability starting at a high pH, and in colonic sugars. This allows the strain to begin growing faster, and presumably to a higher concentration before reaching the colon of *C. difficile* infected patients. These abilities (growth in colonic sugar, and growth in higher pH) should result in a more effective therapeutic via increased doubling of the therapeutic strain in the patient.

Figure 7:
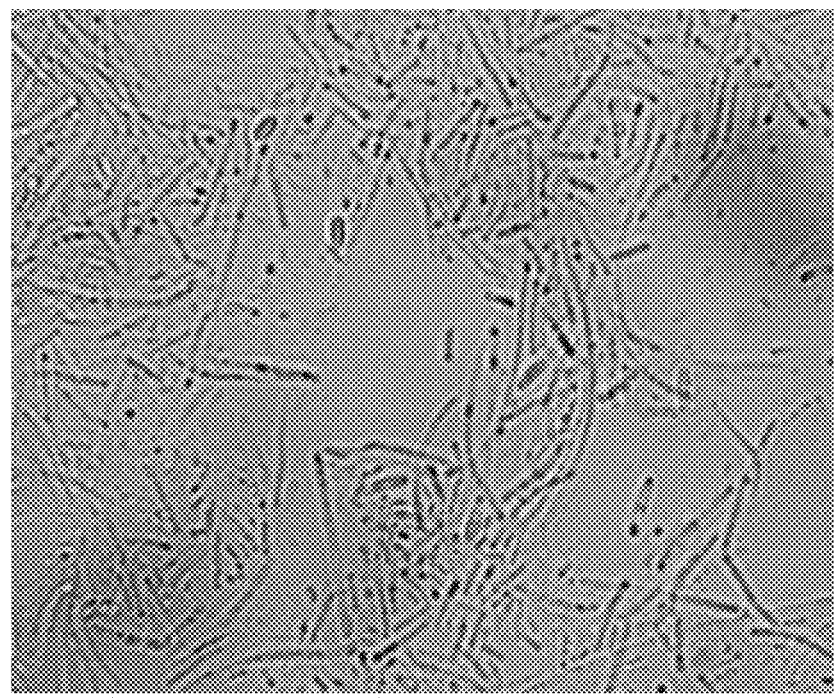
FIG. 7 pictures a close-up of a micrograph taken with a 100× objective from a 5-day old plate of C-9 (comprised of minimal medium). The culture used to grow C-9 was started from a single colony from an anaerobically grown plate on rich medium with a morphology similar to that seen in FIG. 8A. Growth was at 37° C. in the presence of oxygen. Both Lactobacillus and Clostridium morphologies can be seen in the micrograph. Several endospores can be seen near the 5:00 position, as well as freed spores near the 11:00 position.

It should be noted that some chimeric strains show phenotypic plasticity, that is they can express alternate morphologies contingent upon the environment in which they are grown. This is evidence, at least in some cases, that whole genomes or large sections of genomes may be transferred and/or retained, and such cases are possible examples of polyploidy in bacteria. For instance, C-9 morphologically resembled *Lactobacillus* in close-contact colonies within anaerobic environments, but became oligosporogenic in single colonies without close contact to others, creating an endospore resembling *Clostridium* in an aerobic environment (FIG. 6). Spore formation was not observed anaerobically, but more clostridial-like colonies were seen in those colonies which were not in close contact with the others (FIG. 7). In liquid medium, liquid cultures started from either morphology seen in FIGS. 8C and 8D, have a primary morphological phenotype of *Lactobacillus*. However, all cultures started from heat shocked-spores from the aerobic plates were morphologically clostridial even when grown anaerobically. The spore-started cultures displayed about 5% *lactobacillus* forms, but the final pH of the cultures at 48 hours remained roughly at 4.5 versus a final pH of 3.5 seen from non-spore starts. This phenotypic plasticity is indicative of a large volume transfer of genetic information, thus our new term of "chimeric" microbial hybrid.

In both Examples 1 and 2, control gene transfers for both parents were done where only the host parent or only the donor parent was concentrated on to gene transfer filters. No colonies grew, giving evidence that the chimeric traits described in the above examples were not due to spontaneous mutation or recombination between cells of the same species.

Example 3

*Saccharomyces cerevisiae* Var. *boulardii* Sorbitol Metabolism Addition

The desired parental host in this experiment was *Saccharomyces cerevisiae* var. *boulardii*. The phenotype to be acquired was provided by the parental donor, *Metschnikowia reukaffi*, a wild nectar yeast. The desired trait for genetic transfer was sorbitol metabolism, or survival on a protein rich medium with sorbitol as the only carbohydrate source. The nectar yeast donor can grow on this same protein rich medium containing sorbitol at 23-34° C. aerobically. The *Saccharomyces* parent cannot grow on a minimal medium with sorbitol as the sole carbon source; however, it can grow on minimal medium with starch or glucose as the carbon source.

MICs for stressors were determined. *M. reukaffi*'s optimal temperature for growth is 29° C. with an MIC of 35-36° C. *S. cerevisiae* var. *boulardii* has an optimal temperature for growth at 34° C. with an MIC of 44° C. The selected gene transfer medium contained yeast extract along with 2% sorbitol. The donor environmental stressor chosen was slightly higher than MIC results to reduce the chances of it becoming the host. After gene transfer, plates were moved to an aerobic incubator set to 37° C. To summarize, temperature was the gene transfer stressor for *M. reukafii*, while sorbitol as the sole carbon source was the gene transfer stressor for *S. cerevisiae* var. *boulardii*.

There were two experimental groups. One group had both cultures of yeast separately exposed to three rounds of UV light for 2 second intervals followed by 10 minutes of recovery. A negative control for the pre-stressors also kept the strains separated, but without added stress, also at room temperature for 30 minutes. The medium for all cultures was a modified BHI with 2% w/w glucose. Prior to applying the pre-stressors, cultures were grown up in the same modified BHI to an $OD_{600}$ of 1.0 in an aerobic incubator at 33° C. Equivalent starting CFUs for the parental host, *S. cerevisiae* var. *boulardii*, were $3\times10^6$ CFU/ml, for a total volume of 5 ml containing $1.5\times10^7$ cells. Meanwhile, the desired donor, *M. reukafii*, had equivalent CFUs of $2\times10^6$ CFU/ml, for a total volume of 5 ml containing $1\times10^7$ cells.

Following the 30-minute incubation with or without intermittent UV exposure, both parent cultures were mixed together for each condition and filtered on to a sterile nitrocellulose 0.2 μm filter. Filters were then washed via syringe with 10 ml of sterile PBS. Each filter was placed upside down on to a protein containing sorbitol plate. Plates were placed into an aerobic incubator set at 37° C. and were incubated for 72 hours.

After incubation, filters from each condition were removed from agar plates and placed into 1 ml of PBS inside a 1.5 ml microcentrifuge tube. Microcentrifuge tubes containing the filters were vortexed and then spun down at 8000 RFC for 10 minutes. 600 ml of supernatant were removed, and the cell pellet was resuspended in the remaining 400 μl of supernatant. 200 μl of each suspension for each condition was then plated on to a single, fresh, aerobic sorbitol plate containing yeast extract. Once plates were dry, they were placed into an aerobic incubator set to 37° C.

Plates were checked daily for colonies. Additional selection then occurred following 72 hours of growth. Colonies were double streaked on to two different plates for single colonies, one minimal medium plate with sorbitol (no proteins or amino acids), and one rich medium plate containing proteins, *Clostridium difficile* Toxins A and B, along with sorbitol. After two days, single colonies were restreaked again from the toxin containing plates to minimal plates. Only colonies that restreaked, and grew once again to single colonies on the final set of minimal medium plates, were then analyzed.

Results

The frequency of gene transfer resulting in sorbitol metabolizing hybrid was $1.7\times10^{-5}$ for no pre-stressor and $2\times10^{-5}$ using a UV pre-stressor. The extra selection of minimal medium and *C. difficile* Toxins A and B reduced the number of colonies by 10 fold. This is considerably higher than seen in the bacterial gene transfers. What is believed to have been a gene transfer event between the yeast cells was viewed under the microscope as shown in FIGS. 9A-9B; compare the gene transfer micrograph in FIG. 9A with regular budding in FIG. 9B. Eleven chimeric bacterial hybrids were analyzed.

All chimeric microbial hybrids were able to grow at 37° C. on solid media containing yeast extract and 2% sorbitol (data not shown). All eleven chimeric strains were also checked for carbohydrate metabolism in liquid medium using Biomerieux's yeast ID kit (20 C AUX). All Biomerieux growth tests were done at 30-31° C. per their instructions. Only 6 of 11 chimeric yeast hybrids were positive for sorbitol in Biomerieux's medium at 30-31° C. even though all 11 were positive on sorbitol plates at 37° C. Differences in required enzyme temperatures may be responsible for this difference. Just as in Example 2, yeast chimeric hybrids showed carbohydrate metabolism phenotypes from both parents as seen in FIGS. 10A and 10B.

Figure 11:
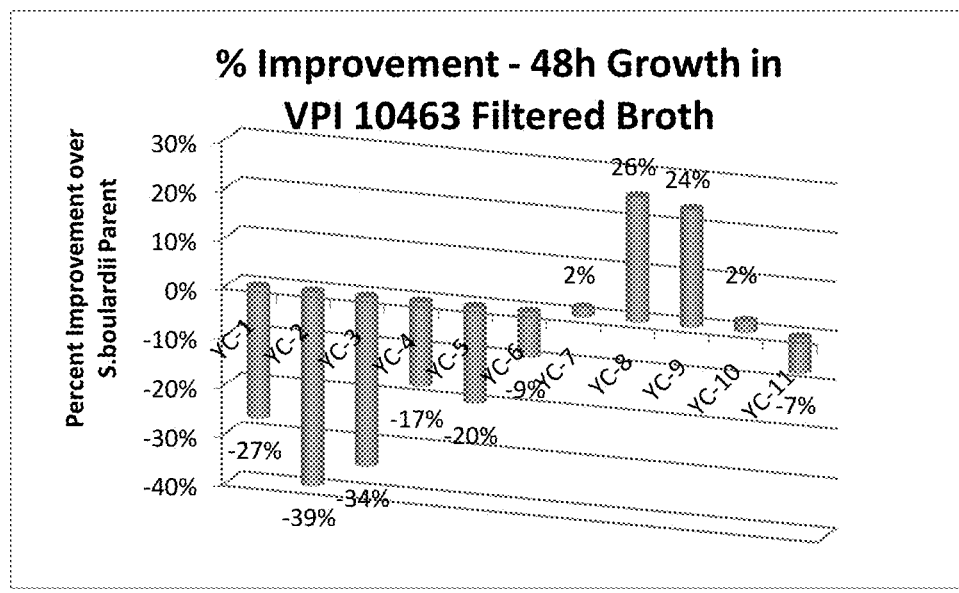
FIG. 11 shows growth in 50% spent broth from Clostridium VPI-10463 and 50% fresh BHI containing 5 g/L yeast medium. Chimeric microbial hybrid strains were grown in filtered broth from an 18-hour old culture of VPI-10463 (containing Toxins A and B). Media was inoculated from overnight cultures with an OD$_{600}$ of approximately 20. Overnight cultures were inoculated at an amount to obtain a starting OD$_{600}$ of 0.05. Improvement in growth via OD$_{600}$ over the Saccharomyces parent can be seen for two of the chimeras. YC-8 and YC-9 showed significantly improved ability to grow in VPI-10463 broth (containing Toxins A and B) at 37° C. for 48 hours.

Both yeast parents are suspected to have different mechanisms of action for Toxin A and B neutralization. Even though toxins were not used directly as an environmental stressor during the gene transfer, they were used for post-gene transfer selection. It was suspected that some chimeras had transferred the toxin neutralizing ability of the *M. reukafii* parent into *S. cerevisiae* var. *boulardii*, while retaining the *S. cerevisiae* var. *boulardii* toxin protease. Although it was not definitively confirmed that both sets of genes for toxin neutralization were present, chimeric microbial hybrids were grown in filtered broth from an 18-hour old culture of VPI-10463 (containing Toxins A and B) from a starting optical density at a wavelength of 600 nm ($OD_{600}$) of 0.05. Improvement in growth via $OD_{600}$ can be seen in FIG. 11. Two of eleven chimeras showed significant improvement growing in VPI-10463 broth at 37° C. for 48 hours.

Example 4

*B. faecale* Amino Acid Auxotrophy Removal Via Gram Negative Donor

The desired parental host was *Bifidobacterium faecale*. The desired phenotype to be transferred was provided by the parental donor, *Grimontella senegalensis*. The desired trait for genetic transfer was amino acid prototrophy, or survival on a minimal medium plate containing no proteins or amino acids.

*G. senegalensis* can grow on minimal medium at 37° C. anaerobically. *B. faecale* cannot grow on a medium without proteins or added amino acids. *B. faecale* can utilize raffinose as a carbon source, whereas *G. senegalensis* cannot.

Selected gene transfer medium was a minimal medium (M9) that contained no proteins or amino acids. The sole carbon source added to the M9 base medium was raffinose. Neither parent could grow on this medium anaerobically at 37° C. No pre-stressors were used.

The medium for growing up parental cultures was a modified RCM with 2% w/w glucose. Prior to applying the pre-stressors, cultures were grown up in the same modified RCM to an $OD_{600}$ of 1.0 in an anaerobic chamber at 35° C. Equivalent starting CFUs for the host, *B. faecale*, were $5\times10^8$ CFU/ml, for a total volume of 5 ml containing $2.5\times10^9$ cells. Meanwhile, the desired donor, *G. senegalensis*, had equivalent CFUs of $2\times10^8$ CFU/ml, for a total volume of 5 ml containing $1\times10^9$ cells.

Both parent cultures were mixed together and filtered on to a sterile nitrocellulose 0.2 μm filter. Filters were then washed via syringe with 10 ml of sterile PBS. Filters were placed upside down on to a deoxygenated, M9 raffinose plate. Plates were incubated in an anaerobic chamber at 37° C. for 72 hours.

After incubation, filters from each condition were placed into 1 ml of PBS inside a 1.5 ml microcentrifuge tube. Microcentrifuge tubes containing the filters were vortexed and then spun down at 8000 RFC for 10 minutes. 600 ml of supernatant were removed, and the cell pellet was resuspended in the remaining 400 μl of supernatant. 200 μl each was spread on to two fresh M9 raffinose plates that were deoxygenated in the chamber for 24 hours prior to plating. Plates were incubated inside an anaerobic chamber at 37° C. for 72-120 hours.

Plates were checked daily for colonies. Single colonies were then re-streaked at 3-5 days post plating from a single colony on to two different plates, one comprised of minimal medium and one comprised of rich medium. After two days, single colonies were restreaked again from the rich medium plates to minimal plates. Only colonies that grew to single colony status on the final set of minimal medium plates were then analyzed.

Results

The frequency of gene transfer resulting in a prototrophic hybrid was much higher than in previous bacterial gene transfers. There were a total of 2,300 colonies for a frequency rate of $1.1\times10^{-6}$. Only three of these chimeric microbial hybrids were analyzed in detail; they were chosen for their different morphologies on a plate.

First, chimeric microbial hybrids were analyzed for carbon consumption via Biomerieux 50 CH. *B. faecale* is not a high acid producer, so some carbon sources may have been missed since the test is ideal for *lactobacillus* and other acid producers like *Grimontella*. Several new carbon sources were able to be metabolized by the chimeras that were not able to be metabolized by either parent. FIG. 12 shows the results of the chimeras versus the parents Biomerieux 50 CH test at 48 hours. The donor strain, gram negative species *G. senegalensis* can metabolize 19 carbon sources and the host strain, gram positive species *B. faecale* can metabolize 12 carbon sources. The resulting *Bifidobacterium* chimeras were able to metabolize up to 18 different carbon sources, 6 more than the wild-type parent.

FIG. 13 shows the result of one chimera, C-5, compared to its parents, *G. senegalensis* (P1) and *B. faecale* (P2). The liquid medium was equivalent to the solid gene transfer medium minus the agar. Bromocresol purple was added to the medium in order to detect growth via pH drop. The light color of the C-5 cultures in FIG. 13 indicates growth in M9 raffinose medium compared to both of its parents, which show no color change post-inoculation. Five milliliter volumes of M9 raffinose medium were inoculated with single colonies from BHI plates and allowed to grow for 48 hours anaerobically at 37° C.

Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention. All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for chromosomal, horizontal gene transfer between two different bacterial parent strains or two different fungal parent strains without the use of a vector, said method comprising combining cells of first and second parent strains together onto a solid or into a liquid growth medium, wherein the growth medium and/or environment surrounding or in contact with the growth medium contains at least one separate stressor for each parent strain, wherein at least one of said stressors does not comprise an antibiotic, wherein each of said stressors is included at a concentration or level that is sufficient to inhibit growth of one of the two parent strains by about 80% to about 100%, wherein each of said parent strains is unable to divide in the presence of said concentration or level of the stressor but wherein DNA transfer is permitted, wherein each of said stressors is included at a concentration or level that permits survival of one of the two parent strains to form single colonies on a solid or liquid medium but that allows no colonies to form in the same conditions for the other parent strain, and wherein a hybrid strain is produced that is a genetic hybrid of the first and second parent strains and that expresses at least one phenotypic trait from genetic material has been transferred from the first parent strain to the second parent strain.

2. The method according to claim 1, wherein the first and second parent strains are different species.

3. The method according to claim 1, wherein the hybrid expresses phenotypic traits from genetic material contributed from both parent strains.

4. The method according to claim 1, wherein the hybrid strain is biotherapeutic for one or more disease conditions.

5. The method according to claim 1, wherein the hybrid strain has increased or decreased fitness for one or more industrial applications, in comparison to the parent strains from which it was derived.

6. The method according to claim 1, wherein the hybrid strain produces a new commodity, in comparison to the parent strains from which it was derived.

7. The method according to claim 1, wherein the hybrid strain has probiotic properties.

8. The method according to claim 1, wherein at least one parent of the hybrid strain is generally recognized as safe (GRAS).

9. The method according to claim 1, wherein the microbial hybrid contains DNA from a parental strain of the bacterial species of *Lactobacillus, Bifidobacterium, Streptococcus, Clostridium, Mycoplasma, Bacillus, Staphylococcus, Lactococcus, Leuconostoc, Pediococcus, Enterococcus, Enterobacteriaceae, Escherichia, Pseudomonas, Bacteroidetes,* or *Actinobacteria.*

10. The method according to claim 1, wherein the hybrid contains DNA from a parental strain of the fungal species of *Saccharomyces, Schizosacchoromyces, Schefferomyces, Zygosaccharomyces, Yarrowia, Pichia, Dekkera, Kluyveromyces, Candida, Metschnikowia,* or *Torulaspora.*

11. The method according to claim 9, wherein the *Lactobacillus* species is *L. plantarum, L. delbrueckii, L. acidophilus, L. brevis, L. casei, L. paracasei, L. sanfranciscensis, L. rhamnosus, L. helveticus, L. curvatus, L. sakei, L. buchneri, L. fermentum,* or *L. reuteri.*

12. The method according to claim 9, wherein the *Bifidobacterium* species is *B. animalis, B. asteroids, B. bifidum, B. breve, B. denticum, B. faecale, B. infantis, B. longum, B. merycicum, B. ruminantium, B. thermacidophilum,* or *B. tsurumiense.*

13. The method according to claim 10, wherein the *Saccharomyces* species is *S. cerevisiae* var. *boulardii, S. cerevisiae, S. pastorianus, S. fragilisis* or *S. bayanus.*

14. A hybrid strain produced according to the method of claim 1.

15. A biotherapeutic hybrid strain produced according to the method of claim 1, wherein the hybrid strain is biotherapeutic for one or more disease conditions.

16. A probiotic hybrid strain produced according to the method of claim 1, wherein the hybrid strain has probiotic properties.

17. A hybrid strain produced according to the method of claim 1, wherein the hybrid strain produces a commodity.

18. A non-naturally occurring hybrid derived from two different bacterial or two different fungal parent strains or species without the use of recombinant DNA technology according to the method of claim 1.

19. The method according to claim 1, wherein neither of said separate stressors for the first parent strain and for the second parent strain comprises an antibiotic.

20. The method according to claim 1, wherein at least one of said separate stressors for the first and/or second parent strain is selected from an antifungal substance, an organic compound, a solvent, high temperature, low temperature, ultraviolet light, an osmotic stressor, an inorganic chemical, ionizing radiation, composition of atmospheric gas, a vitamin or co-factor, absence of a vitamin or co-factor, an acid, a base, a carbohydrate source, a nitrogen source, a biological toxin, a peptide, a preservative substance, an herbicide, a fungicide, a pesticide, or a filtrate of another microbe's spent fermentation broth.

21. The method according to claim 1, wherein said separate stressors for both the first and second parent strains are selected from an antifungal substance, an organic compound, a solvent, high temperature, low temperature, ultraviolet light, an osmotic stressor, an inorganic chemical, ionizing radiation, composition of atmospheric gas, a vitamin, or co-factor, absence of a vitamin or co-factor, an acid, a base, a carbohydrate source, a nitrogen source, a biological toxin, a peptide, a preservative substance, an herbicide, a fungicide, a pesticide, or a filtrate of another microbe's spent fermentation broth.

* * * * *